(12) United States Patent
Takehara et al.

(10) Patent No.: US 11,389,121 B2
(45) Date of Patent: Jul. 19, 2022

(54) IMAGING TABLE, MAMMOGRAPHY APPARATUS IMAGING TABLE AND MANUFACTURING METHOD THEREFOR, AND MAMMOGRAPHY APPARATUS

(71) Applicant: Toray Industries, Inc., Tokyo (JP)

(72) Inventors: Tomohiro Takehara, Ehime (JP); Mitsushige Hamaguchi, Nagoya (JP); Masato Honma, Ehime (JP)

(73) Assignee: Toray Industries, Inc., Tokyo (JP)

( * ) Notice: Subject to any disclaimer, the term of this patent is extended or adjusted under 35 U.S.C. 154(b) by 27 days.

(21) Appl. No.: 16/982,677

(22) PCT Filed: Mar. 20, 2019

(86) PCT No.: PCT/JP2019/011937
§ 371 (c)(1),
(2) Date: Sep. 21, 2020

(87) PCT Pub. No.: WO2019/182076
PCT Pub. Date: Sep. 26, 2019

(65) Prior Publication Data
US 2021/0106293 A1 Apr. 15, 2021

(30) Foreign Application Priority Data

Mar. 23, 2018 (JP) .............................. JP2018-055836
Mar. 23, 2018 (JP) .............................. JP2018-055840

(51) Int. Cl.
*A61B 6/04* (2006.01)
*B29C 70/00* (2006.01)
(Continued)

(52) U.S. Cl.
CPC .......... *A61B 6/0442* (2013.01); *A61B 6/0414* (2013.01); *B29C 43/10* (2013.01);
(Continued)

(58) Field of Classification Search
CPC ....... A61B 6/04; A61B 6/0407; A61B 6/0414; A61B 6/0442; A61B 6/42; A61B 6/4283;
(Continued)

(56) References Cited

U.S. PATENT DOCUMENTS 5,960,057 A 9/1999 Majewski et al.
6,995,099 B1 2/2006 Nishimura et al.
(Continued)

FOREIGN PATENT DOCUMENTS

JP 60236634 A 11/1985
JP 2003207864 A 7/2003
(Continued)

OTHER PUBLICATIONS

Extended European Search Report for European Application No. 19 770 384.6, dated Nov. 11, 2021, 9 pages.
(Continued)

*Primary Examiner* — Anastasia Midkiff
(74) *Attorney, Agent, or Firm* — RatnerPrestia

(57) ABSTRACT

An imaging table for a mammography apparatus is formed by a planar body and is to be supported in a cantilever state on a body of the mammography apparatus. At least an X-ray irradiation surface in the planar body has at least one of the following configurations (1) and (2): (1) the X-ray irradiation surface is formed by a carbon fiber composite material including a unidirectional carbon fiber composite material containing carbon fibers and a matrix resin, the carbon fibers being aligned in one direction; and (2) the X-ray irradiation surface is formed by a skin material and a resin sheet, the skin material including a carbon fiber composite material containing continuous fibers and a matrix resin, the resin sheet being disposed on an inner layer side from the skin material.

14 Claims, 18 Drawing Sheets

(51) Int. Cl.
*B29C 70/06* (2006.01)
*B29C 43/10* (2006.01)
*B32B 5/24* (2006.01)
*B32B 27/04* (2006.01)
*B32B 5/02* (2006.01)
*B32B 5/12* (2006.01)

(52) U.S. Cl.
CPC .............. *B29C 70/00* (2013.01); *B29C 70/06* (2013.01); *B32B 5/024* (2013.01); *B32B 5/12* (2013.01); *B32B 5/245* (2013.01); *B32B 27/04* (2013.01); *B32B 2260/023* (2013.01); *B32B 2262/106* (2013.01); *B32B 2535/00* (2013.01)

(58) Field of Classification Search
CPC ....... A61B 6/44; A61B 6/502; A61B 2560/04; A61B 2560/0406; A61B 2560/06; A61B 2562/16; A61B 2562/17; B29C 45/17; B29C 45/1723
See application file for complete search history.

(56) References Cited

U.S. PATENT DOCUMENTS

| | | | | |
|---|---|---|---|---|
| 8,331,536 | B2* | 12/2012 | Shaw | ..................... A61B 6/502 378/154 |
| 2007/0189447 | A1* | 8/2007 | Holler | ................... G03B 42/02 378/37 |
| 2011/0268255 | A1 | 11/2011 | Ramsauer | |
| 2015/0164449 | A1 | 6/2015 | Ko et al. | |
| 2017/0239895 | A1* | 8/2017 | Takehara | ................ B32B 27/12 |
| 2019/0054706 | A1* | 2/2019 | Takehara | ................... C08J 5/24 |
| 2019/0208654 | A1* | 7/2019 | Hamaguchi | ............... B29B 9/14 |
| 2019/0237862 | A1* | 8/2019 | Hamaguchi | ............... B32B 5/12 |

FOREIGN PATENT DOCUMENTS

| | | |
|---|---|---|
| JP | 2005313613 A | 11/2005 |
| JP | 2009230000 A | 10/2009 |
| JP | 2010035622 A | 2/2010 |
| JP | 2010039267 A | 2/2010 |
| JP | 5126405 B2 | 1/2013 |
| JP | 2016022061 A | 6/2016 |
| JP | 2017122382 A | 7/2017 |
| WO | 0056539 A1 | 9/2000 |

OTHER PUBLICATIONS

International Search Report and Written Opinion for International Application No. PCT/JP2019/011937, dated Jun. 4, 2019, 7 pages.

* cited by examiner

Cross Section in y-z Plane

Cross Section in y-z Plane

Fiber Direction

Cross Section in x-z Plane

Cross Section in y-z Plane

Cross Section in y-z Plane

Cross Section in y-z Plane

Cross Section in x-z Plane

Cross Section in y-z Plane

Cross Section in x-z Plane

Cross Section in y-z Plane

Cross Section in y-z Plane

Cross Section in x-z Plane

Cross Section in y-z Plane

Cross Section in x-z Plane

Cross Section in y-z Plane

IMAGING TABLE, MAMMOGRAPHY APPARATUS IMAGING TABLE AND MANUFACTURING METHOD THEREFOR, AND MAMMOGRAPHY APPARATUS

CROSS REFERENCE TO RELATED APPLICATIONS

This is the U.S. National Phase application of PCT/JP2019/011937, filed Mar. 20, 2019, which claims priority to Japanese Patent Application No. 2018-055836, filed Mar. 23, 2018, and Japanese Patent Application No. 2018-055840, filed Mar. 23, 2018, the disclosures of each of these applications being incorporated herein by reference in their entireties for all purposes.

FIELD OF THE INVENTION

The present invention relates to an imaging table which is supported in a cantilever state on an X-ray imaging apparatus, and an imaging table for a mammography apparatus which table is supported in a cantilever state on a body of the mammography apparatus.

BACKGROUND OF THE INVENTION

A common mammography apparatus obtains image data by X-ray imaging of a breast of an examinee in order to examine the breast (Patent Literature 1). The mammography apparatus is provided with an imaging table and a pressing plate for pressing the breast in order to obtain image data high in contrast or resolution with little geometric blur or defocusing caused by body motion. The breast supported on the imaging table is pressed by the pressing plate to be retained at a uniform thickness, and then the breast is irradiated with X-rays, and the X-rays transmitted by the breast are detected to generate image data.

The imaging table is internally provided with an X-ray detection portion for detecting X-rays penetrating the pressing plate and a breast as a subject to be imaged. Therefore, the imaging table is formed by a material excellent in X-ray transparency. In addition, the subject is pressed so as to have uniform thickness by the pressing plate during imaging. Accordingly, an external force caused by the pressing plate also acts on the imaging table. In the case where the imaging table is easily deformed by the external force, obtained image data may deteriorate in contrast or resolution. Therefore, the imaging table is typically formed by a material excellent in rigidity. From the aforementioned background, a carbon fiber reinforced composite material (carbon composite material) excellent in X-ray transparency and high in rigidity is used suitably for an imaging table for a mammography apparatus as described in Patent Literature 1.

For mammography, besides the aforementioned imaging method using the imaging table, another method for directly imaging a subject placed on a cassette is also disclosed (Patent Literature 2). Since this imaging method uses a thin and rectangular cassette, the imaging method can avoid an increase in weight, and thus the handleability can be improved. In addition, the front member to be irradiated with X-rays is integrated with an outer circumferential frame member. Thus, there is an effect that deformation during imaging can be inhibited. Here Patent Literature 2 suggests that the front member is constituted by a laminate which is obtained by a plurality of layers (carbon fiber layers) each having a large number of carbon fiber filaments are arrayed in one direction are put on top of one another and impregnated with a thermosetting resin.

PATENT LITERATURE

Patent Literature 1: JP-A-2010-35622
Patent Literature 2: JP-A-2010-39267

SUMMARY OF THE INVENTION

Here, it is necessary to further improve the contrast and resolution of an image taken by mammography in order to detect a lesion in an early stage, and there is need for improvement of X-ray transparency in an imaging table for a mammography apparatus or increase in rigidity thereof.

However, in the mammography apparatus described in Patent Literature 1, it is indeed disclosed that the imaging table is formed by carbon fibers, but there is no disclosure or no suggestion as to requirements thereof, such as the form of the fibers or the configuration of the region formed by the carbon fibers.

Here, an imaging table for a mammography apparatus commercially available as a product has a hollow box-like shape. Even when a carbon fiber composite material is used, the material is practically limited to a material having a woven fabric form because it is excellent in shape followability. According to such a carbon woven fabric composite material, carbon fibers having waviness forms a woven texture in a matrix resin. When a specific shape is imparted to the carbon woven fabric composite material, the woven texture is rearranged to show excellent shape followability.

However, due to the waviness of the carbon fibers in the carbon woven fabric composite material, there is a problem that the potential of elasticity or strength belonging to the carbon fibers cannot be exerted sufficiently. In addition, the waviness restricts the arrangement of the fibers so that there is an upper limit of the volume content of the carbon fibers in the carbon woven fabric composite material. Therefore, the imaging table for a mammography apparatus using the carbon woven fabric composite material has a limitation in reduction in thickness for X-ray transparency or improvement of mechanical properties for rigidity. In addition, the carbon woven fabric composite material is excellent in rigidity and strength due to carbon fibers included therein, but in order to attain the excellent rigidity and strength, it is necessary to mold the carbon woven fabric composite material without any air gap among the carbon fibers and the matrix resin. There is a limit to reduce weight in the X-ray transparency direction affecting the X-ray transparency to improve the X-ray transparency.

On the other hand, in the invention according to Patent Literature 2, a medical cassette capable of imaging by mammography is described. A plurality of layers each having a large number of carbon fiber filaments arrayed unidirectionally are used as a front member, by which excellent rigidity is given to the cassette. In addition, the front panel has a flat plate-like shape so that a core material in light weight can be included therein. Thus, the cassette can have a form in which the X-ray transparency can be improved.

However, the medical cassette is a container which is loaded with a film to be used for imaging with X-rays. The characteristic required in the medical cassette is different from that in an imaging table for a mammography apparatus supported in a cantilever state on the mammography apparatus. The medical cassette is constituted by the flat plate-like front member, the back member and the frame forming the standing wall. Therefore, on the conditions where a load acts on a central face as in imaging by mammography, the standing wall portion is likely to be deformed so that it is likely that the medical cassette may be broken in the boundary between the front panel forming an X-ray irradiation surface and the frame forming the standing wall.

In addition, the cassette typically has a thin and rectangular body. There is a limit in the proportion with which the core material is contained. In addition, when the medical cassette is supported like a cantilever and used as an imaging table, the medical cassette is deformed easily due to a load received from a pressing plate. Thus, the contrast or resolution of obtained image data may deteriorate. Further, there is a fear that the standing wall portion biting into an examinee may give a feeling of discomfort to the examinee during imaging by mammography. In addition, in the case where the number of fibers arrayed unidirectionally increases, there is a fear that when a member having a complicated shape is molded, the fibers cannot follow the complicated shape satisfactorily. With respect to this point, in the medical cassette, the front member and the back member can be separated and molded separately as described in Patent Literature 2. However, it is not considered to mold a plurality of members separately to obtain an imaging table for a mammography apparatus. It has been typically considered that molding using fibers arrayed unidirectionally is not easy.

Therefore, the present invention has been developed in consideration of the aforementioned problems. An object of the invention is to provide a thin and rigid imaging table, and a thin and rigid imaging table for a mammography apparatus. Another object of the present invention is to provide an imaging table for a mammography apparatus capable of attaining high X-ray transparency and high rigidity.

To solve the above problem, the imaging table in the present invention has the following configuration:

an imaging table to be supported in a cantilever state on an X-ray imaging apparatus, the imaging table including a planar body including an opening portion in a surface to be connected to the apparatus, and a coupling portion to be connected to the apparatus, in which:

at least an X-ray irradiation surface in the planar body includes a unidirectional carbon fiber composite material containing carbon fibers and a matrix resin, the carbon fibers being aligned in one direction; and the coupling portion is bonded to a region formed by the unidirectional carbon fiber composite material.

Further, the imaging table for a mammography apparatus in the present invention has the following configuration:

an imaging table for a mammography apparatus, which is to be supported in a cantilever state on a body of the mammography apparatus, in which:

at least an X-ray irradiation surface of the imaging table is formed by a carbon fiber composite material; and the carbon fiber composite material includes a unidirectional carbon fiber composite material containing carbon fibers and a matrix resin, the carbon fibers being aligned in one direction.

Further, the imaging table for a mammography apparatus in the present invention has the following configuration:

an imaging table for a mammography apparatus, which is formed by a planar body and is to be supported in a cantilever state on a body of the mammography apparatus, in which:

at least an X-ray irradiation surface in the planar body is formed by a skin material and a resin sheet, the skin material including a carbon fiber composite material containing continuous fibers and a matrix resin, the resin sheet being disposed on an inner layer side from the skin material.

Further, the method for manufacturing an imaging table for a mammography apparatus in the present invention has the following configuration:

A method for manufacturing an imaging table for a mammography apparatus, including the following steps (I) and (II):

Step (I): a step of imparting a shape of a single-surface mold to a base material including carbon fibers (A) and a thermosetting resin (B), the carbon fibers including continuous fibers; and Step (II): a step of covering a space including the single-surface mold and the base material with a flexible film, and applying heat and pressure.

In the present invention, it is possible to provide an imaging table in which, due to reduced thickness and high rigidity, an exposure dose of an examinee can be reduced by an effect of improvement of X-ray transparency caused by the reduced thickness, and deflection caused by a load applied during imaging can be inhibited by an effect of the high rigidity, thereby improving the quality of an image taken therefrom.

In addition, in the present invention, it is possible to provide an imaging table for a mammography apparatus in which, due to reduced thickness and high rigidity, an exposure dose of an examinee can be reduced by an effect of improvement of X-ray transparency caused by the reduced thickness, and deflection caused by a load applied during imaging can be inhibited by an effect of the high rigidity, thereby improving the quality of an image taken therefrom.

In addition, it is possible to provide an imaging table for a mammography apparatus in which a resin sheet in light weight is included so that X-ray transparency can be improved to reduce an exposure dose of an examinee, and a skin material including a carbon fiber composite material is included so that high rigidity can be exhibited to inhibit deflection caused by a load applied during imaging, thereby improving the quality of an image taken therefrom.

DETAILED DESCRIPTION OF EMBODIMENTS OF THE INVENTION

An imaging table according to an embodiment of the present invention is an imaging table supported in a cantilever state on an X-ray imaging apparatus, and characterized as follows.

The imaging table includes a planar body including an opening portion in a surface to be connected to the X-ray imaging apparatus, and a coupling member to be connected to the apparatus. At least an X-ray irradiation surface in the planar body contains a unidirectional carbon fiber composite material including carbon fibers aligned in one direction, and a matrix resin. The coupling member is bonded to a region which is formed by the unidirectional carbon fiber composite material. The application of the imaging table is not limited as long as it is supported in a cantilever state on an X-ray imaging apparatus. For example, the imaging table may be an imaging table for a mammography apparatus.

The mammography apparatus according to the embodiment of the present invention is formed by connecting the imaging table for the mammography apparatus to a body of the mammography apparatus. The imaging table for the mammography apparatus in the present invention will be described below.

In the imaging table for the mammography apparatus according to the embodiment of the present invention, the unidirectional carbon fiber composite material is used for at least the X-ray irradiation surface so that the rigidity can be made higher than that in a carbon fiber woven fabric composite material in the related art. Accordingly, when bending rigidity, which is a property affecting a deflection amount, is used as a design index, the unidirectional carbon fiber composite material can be made thinner in sheet thickness than in the case of carbon fiber woven fabric composite material. Therefore, attenuation of intensity until X-rays transmitted by the imaging table for the mammography apparatus reaches an X-ray detector inside the imaging table can be reduced. That is, X-ray transparency can be improved to reduce the exposure dose of an examinee.

Here, the sheet thickness is a sheet thickness of the X-ray irradiation surface contributing to the X-ray transparency, and it is preferably 0.5 mm or more and 5.0 mm or less, and more preferably 0.8 mm or more and 3.5 mm or less. Any ones of the aforementioned upper and lower limits may be combined as a range. In the case where the sheet thickness is less than 0.5 mm, rigidity as an imaging table cannot be secured. Thus, there is a fear that the imaging table may be deformed easily during imaging. In the case where the sheet thickness exceeds 5.0 mm, the X-ray transparency deteriorates so that the intensity of irradiation with X-rays must be increased. Thus, there is a fear that the exposure dose of an examinee per imaging may increase.

Figure 1:
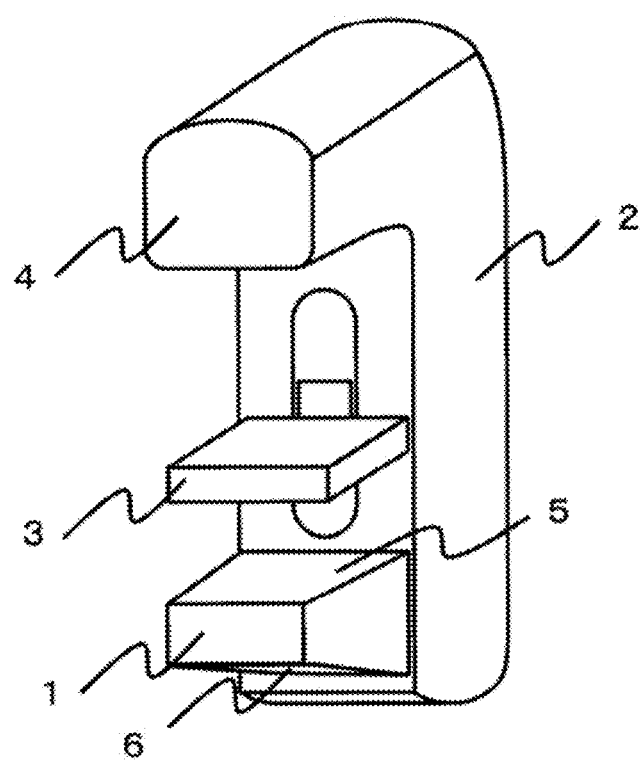
FIG. 1 is a block diagram showing a configuration of a mammography apparatus according to an embodiment of the present invention.

The body of the mammography apparatus includes an X-ray generation portion and a pressing plate. Those parts may be laid out as illustrated in FIG. 1. A mammography apparatus imaging table 1 according to the embodiment of the present invention is supported in a cantilever state on a mammography apparatus body 2. In addition, the mammography apparatus shown in FIG. 1 has the mammography apparatus body 2, the mammography apparatus imaging table 1, a pressing plate 3, and an X-ray generation portion 4. The mammography apparatus imaging table 1 has an X-ray irradiation surface 5 and a bottom surface 6. In addition, the mammography apparatus imaging table 1 according to the embodiment of the present invention is formed by a planar body in which length of each side forming each surface is much longer than the sheet thickness. The mammography apparatus imaging table 1 typically has an approximately box-like shape with a cavity in its inside. An X-ray detector is often provided inside the cavity. The X-ray detector may be connected to the body of the mammography apparatus directly or may be fixed into the imaging table and connected to the mammography apparatus body 2 through wiring.

In addition, the X-ray irradiation surface is a flat face region included in a top surface of the imaging table according to the embodiment of the present invention. The flat face region may be the whole of the top surface of the imaging table or may be a part thereof. In terms of X-ray transparency and rigidity, the X-ray irradiation surface is formed by a carbon fiber composite material. In addition, the X-ray irradiation surface may further include a resin sheet.

Figure 21:
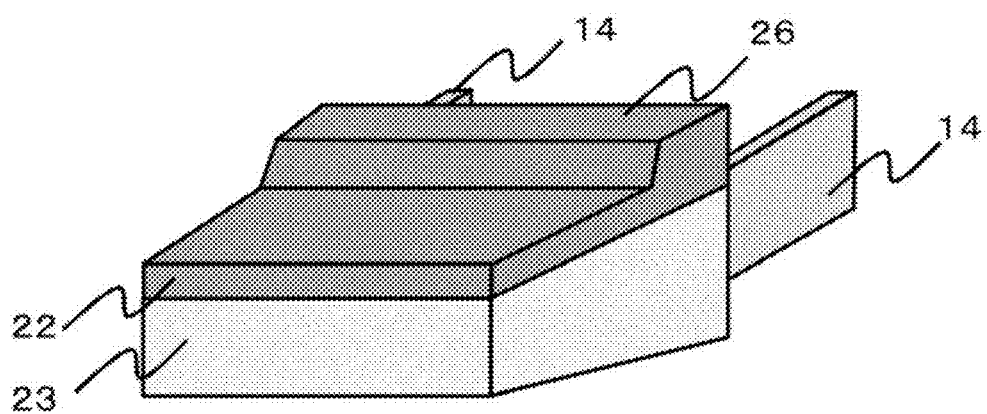
FIG. 21 is a schematic view showing an example of the external appearance of the imaging table for the mammography apparatus according to the embodiment of the present invention.

More preferably, a step portion may be provided in a top surface region other than the X-ray irradiation surface. In the case where such a shape is provided, the step portion functions as a standing wall so that deflection caused by a load of the pressing plate during imaging by mammography can be inhibited. In addition, the region where the X-ray detector etc. can be received inside the imaging table can be expanded. The position where the step portion is provided may be a connection surface to the apparatus by way of example (FIG. 21).

The imaging table for the mammography apparatus according to the embodiment of the present invention is configured thus. In this configuration, the light resin sheet is disposed on the inner layer side of a skin material containing a carbon fiber composite material. Therefore, as compared with a configuration in which the imaging table is formed by the carbon fiber composite material alone, attenuation of intensity until X-rays transmitted by the imaging table for the mammography apparatus reaches the X-ray detector inside the imaging table can be inhibited, that is, the X-ray transparency can be improved to reduce the exposure dose of an examinee. In addition, due to the skin material formed by the carbon fiber composite material containing continuous fibers, a major part of a load applied during imaging can be received by the skin material which is high in rigidity. Thus, it is possible to improve the X-ray transparency while maintaining the rigidity.

It is preferable that at least the X-ray irradiation surface in the planar body is formed by a sandwich structure in which the skin material containing the carbon fiber composite material is disposed on each of the opposite sides of the core material containing the resin sheet. Although the structure of the planar body is either a canape structure in which the skin material is present on only one side of the outermost surfaces, or a sandwich structure in which the skin material is present on the opposite sides of the surfaces of the imaging table. In order to attain high rigidity and high X-ray transparency, the sandwich structure in which the X-ray irradiation surface includes the skin layer composed of the carbon fiber composite material and the core material composed of the resin sheet is preferred.

Typically, as the sheet thickness is increased, the bending rigidity giving influence to the deflection amount is improved to have an effect of reducing the deflection amount.

However, if the sheet thickness is increased simply, there is a demerit in terms of X-ray transparency. In the case where the configuration in which the resin sheet excellent in X-ray transparency is used as the core material is used as in the present invention, it is possible to attain high X-ray transparency and high rigidity.

The carbon fiber composite material forming the X-ray irradiation surface preferably has a specific bending elastic modulus of 2.50 or higher. The specific bending elastic modulus is expressed as $Eb^{1/3} \times p^{-1}$ where Eb designates the bending elastic modulus and p designates the density. The specific bending elastic modulus of the carbon fiber composite material is preferably 2.50 or higher, because the bending elastic modulus is relatively high and the density is relatively low, which can keep good balance between difficulty in deformation and high X-ray transparency suitably. On the other hand, the upper limit of the specific bending elastic modulus is not particularly limited. In the case where the specific bending elastic modulus is set at 20.00 or lower, the balance between the effect of improving the X-ray transparency and the bending elastic modulus is suitably excellent.

The carbon fiber composite material contains carbon fibers as continuous fibers, and a matrix resin. Examples of the form of the continuous fibers include a woven fabric form in which a woven texture is formed by continuous fibers, and a form in which continuous fibers are aligned in one direction. Each of those forms may be used alone or in lamination, or the two kinds may be used in lamination.

The continuous fibers are fibers which are aligned in a continuous state as a fiber bundle without being cut off into a short-fiber state. Here, the short fiber designates a fiber having a length of 100 mm or shorter. Among the forms, in order to obtain a uniform in-plane distribution of the X-ray transparency, that is, in order to reduce a variation in in-plane density, it is preferable to use the form in which continuous fibers are aligned in one direction because the continuous fibers can be arranged easily without any gap. In addition, in terms of shape followability, the skin material may be formed in combination of the form in which discontinuous fibers are arrayed unidirectionally or a form in which discontinuous fibers are dispersed.

Preferably the imaging table for the mammography apparatus according to the embodiment of the present invention has a configuration further including a carbon fiber woven fabric composite material containing a woven fabric of carbon fibers and a resin, in addition to the unidirectional carbon fiber composite material.

Due to such a configuration, it is possible to obtain both the effect of shape followability attributed to the carbon fiber woven fabric composite material and the effect of high rigidity attributed to the unidirectional carbon fiber composite material. For example, a large amount of the unidirectional carbon fiber composite material is used in the top surface of the imaging table, which contributes to X-ray transparency or rigidity, or in order to make much account to designability, the carbon fiber woven fabric composite material is used in the outermost layer.

It is preferable that the carbon fiber woven fabric composite material containing a woven fabric of carbon fibers and a resin is included in the outermost layer of the carbon fiber composite material. As the proportion of the carbon fiber woven fabric composite material is increased, shape molding can be achieved more easily. On the other hand, the unidirectional carbon fiber composite material is contained in the X-ray irradiation surface where thickness should be reduced but rigidity should be increased. As the proportion of the unidirectional carbon fiber composite material is increased, the aforementioned properties can be attained easily.

The mammography apparatus may have a gentle curved face in terms of designability or have a handle in order to allow an examinee to keep his/her posture during imaging. In the same manner, the imaging table for the mammography apparatus may be also designed to have a gentle curved face excluding the X-ray irradiation surface engaging in mammography imaging or corner portions (parts bent from the X-ray irradiation surface) of the standing wall surface (standing wall surface opposed to the body of the mammography apparatus) which will touch the examinee, in order to relax pain of the examinee who touches the standing wall surface.

In a more preferred form, the carbon fiber woven fabric composite material is contained in the outermost layer of the carbon fiber composite material. In addition, in a more preferred form, the carbon fiber woven fabric composite material is contained in the outermost layer of the planar body.

In the case where the outermost surface which will touch the bare skin of the examinee has such a configuration, the carbon fibers in the carbon fiber woven fabric composite material can be prevented from fluffing as compared with the unidirectional carbon fiber composite material, even if the resin deteriorates due to a change with time such as exposure to an antiseptic solution in an operating environment. Thus, a stimulus to the examinee can be relaxed. From this point of view, it is particularly preferable that the outermost layer of the X-ray irradiation surface is formed by the carbon fiber woven fabric composite material, and the unidirectional fiber composite material is disposed in inner layers.

<Materials>

The carbon fiber composite material according to the embodiment of the present invention preferably contains carbon fibers and a matrix resin.

The carbon fibers are not particularly limited, but examples of the carbon fibers include polyacrylonitrile (PAN) based fibers, pitch based carbon fibers, etc. A single kind of those fibers may be used, or two or more kinds of them may be used together. Among them, the PAN based carbon fibers is more preferable in terms of balance between strength and elasticity in the carbon fiber composite material obtained therefrom. The strand elastic modulus of the carbon fibers is preferably 200 GPa or more, more preferably 220 GPa or more, and even more preferably 240 GPa or more. If the strand elastic modulus of the carbon fibers is less than 200 GPa, there is a case that intended properties cannot be obtained in the carbon fiber composite material obtained therefrom.

The matrix resin is not particularly limited, but either a thermosetting resin or a thermoplastic resin may be used. In the case where the matrix resin is a thermosetting resin, the thermosetting resin is cured to serve as the matrix resin due to heating during molding, and, if necessary, due to further heating to a temperature high enough to cure the thermosetting resin after the molding. In the case where the matrix resin is a thermoplastic resin, the resin melted by heating during molding is cooled and solidified to serve as the matrix resin.

Examples of the thermosetting resin include epoxy resin, vinyl ester resin, phenolic resin, unsaturated polyester resin, etc. Any thermosetting resin may be used as long as it can cause a crosslinking reaction due to heat, thereby forming a three-dimensional crosslinked structure at least partially. On the other hand, a prepreg can be used as a molding base material for forming the carbon fiber composite material. As a form of the thermosetting resin in the prepreg, the thermosetting resin is preferably in a semi-cured state excellent in tackiness so that the prepreg can be bonded in a pressed manner to another prepreg or to a mold when the prepreg is laminated. Among the thermosetting resins, the epoxy resin is preferred in consideration of the tackiness in a pasting step and the mechanical characteristic as a molded product obtained therefrom.

Preferred examples of the thermoplastic resin include propylene resin, polyethylene resin, polyamide resin, polyester resin, polyarylene sulfide resin, polyphenylene sulfide resin, polyether ketone resin, polyether ether ketone resin, polyether ketone ketone resin, polyether sulfone resin, polyimide resin, polyamide imide resin, polyether imide resin, and polysulfone resin. In addition, a cyclic oligomer which is a precursor of any one of those resins is also used preferably. Among them, a resin excellent in chemical resistance is preferably selected in consideration of cleaning with an antiseptic from the viewpoint of operation of the imaging table for the mammography apparatus.

The unidirectional carbon fiber composite material according to the embodiment of the present invention includes layers each including carbon fibers aligned in one direction and a matrix resin. The unidirectional carbon fiber composite material may be configured by a single layer or may be configured by a laminate in which two or more layers are laminated. In addition, in the case where two or more layers each including carbon fibers aligned in one direction and a matrix resin are laminated, the unidirectional carbon fiber composite material may have a configuration in which orientation directions of the carbon fibers are shifted among the layers desirably. In terms of the yield in cutting out the material from a sheet-like base material, the unidirectional carbon fiber composite material preferably has a lamination configuration in which the orientation directions of the carbon fibers are shifted from one layer to another by 90°. In addition, in a lamination configuration preferred in terms of isotropy, the orientation directions of the carbon fibers are shifted from one layer to another by 30° to 60°.

Preferred examples of such lamination configurations include a lamination configuration in which the orientation directions of the continuous fibers are shifted from one layer to another by 45°, and a lamination configuration in which the orientation directions of the continuous fibers are shifted from one layer to another by 60°.

The carbon fiber woven fabric composite material according to the embodiment of the present invention includes a sheet-like material obtained by weaving carbon fibers, and a matrix resin. The carbon fiber woven fabric composite material typically includes a layer structure, which may be constituted by a single layer or may be constituted by a laminate in which two or more layers are laminated. Examples of the woven texture of the carbon fibers include a plain weave, a twill weave, a satin weave, etc. Among them, the twill weave is preferred in terms of shape followability and X-ray transparency.

A material included in the resin sheet according to the embodiment of the present invention may be either a thermosetting resin or a thermoplastic resin. The material is not particularly limited as long as its density is lower than that of the carbon fiber composite material. Examples of the thermosetting resin include epoxy resin, vinyl ester resin, phenolic resin, thermosetting polyimide resin, polyurethane resin, urea resin, melamine resin, bismaleimide resin, acrylic resin, etc. In addition to the epoxy resin alone, a copolymer of epoxy resin and a thermosetting resin, a modified one of epoxy resin, a resin in which two or more kinds of epoxy resins are blended, etc. can be used. Examples of the thermoplastic resin include polypropylene resin, polyethylene resin, polycarbonate resin, polyamide resin, polyester resin, polyarylene sulfide resin, polyphenylene sulfide resin, polyether ketone, polyether ether ketone resin, polyether ketone ketone resin, polyether sulfone resin, polyimide resin, polyamide imide resin, polyether imide resin, polysulfone resin, polystyrene resin, acrylonitrile-butadiene-styrene (ABS) resin, polyvinyl chloride resin, and polymethacrylimide resin. In addition, a cyclic oligomer which is a precursor of any one of those resins is also used preferably. In addition, the resin sheet may contain a filler such as carbon fibers or glass fibers in order to enhance the mechanical characteristic. In the case where a thermosetting resin is used, when the thermosetting resin which has not been cured yet is molded, there is a fear that the thermosetting resin flows and it cannot be molded. Therefore, the thermosetting resin may be made into a cured sheet which has been molded into a desired shape in advance. In terms of moldability, a resin sheet using a thermoplastic resin as a material is used preferably because it can follow a shape due to heat. Further, even in the case where the resin sheet uses a thermoplastic resin as a material, the sheet which has been thermally shaped into a desired shape in advance may be molded.

In addition, the resin sheet according to the embodiment of the present invention preferably includes discontinuous reinforced fibers which are dispersed like substantial monofilaments and at random. Due to such a form, the discontinuous reinforced fibers dispersed like substantial monofilaments can minimize weak portions at ends of a fiber bundle of the discontinuous reinforced fibers in addition to the effect of improving the mechanical characteristic, as compared with a case where the resin sheet is formed by a resin alone. Thus, excellent reinforcing efficiency can be exhibited. In addition, due to the discontinuous reinforced fibers dispersed at random, isotropy can be dynamically exhibited to substantially prevent a performance change caused by a wrong arrangement in molding, which is an expected mistake. Thus, the reliability of a product is improved. This is also preferable in terms of X-ray transparency, because a homogenous image can be obtained easily.

Here, the substantial monofilaments designate that a single filament of discontinuous reinforced fibers exists as less than 500 thin-fineness strands. The single filament diameter of the discontinuous reinforced fibers is preferably 20 μm or less, and more preferably 10 μm or less in terms of reflection on an X-ray fluoroscopic image. If the single filament diameter is more than 20 μm, it is likely to affect the reflection on the X-ray fluoroscopic image. In addition, the kind of the discontinuous reinforced fibers is not particularly limited, but carbon fibers are preferred in terms of X-ray transparency and the reinforcing effect.

In addition, the resin sheet according to the embodiment of the present invention preferably includes a resin, discontinuous reinforced fibers, and voids. Due to such a form, the mechanical characteristic can be maintained by the discontinuous reinforced fibers contained therein, and the density can be reduced by the voids contained therein, thereby improving the X-ray transparency. Here, the voids designate spaces formed in such a manner that the discontinuous reinforced fibers covered with the resin serve as columnar supports, which are superimposed on one another or intersect one another to form the spaces. In addition, the content of the voids is within a range of 10% by volume or higher and 99% by volume or lower. If the content of the voids is lower than 10% by volume, the density of the resin sheet may increase to reduce the effect of improving the X-ray transparency. On the contrary, when the content of the voids exceeds 99%, the thickness of the resin covering the discontinuous reinforced fibers may be reduced so that the resin sheet is insufficiently reinforced by the discontinuous reinforced fibers. As a result, the mechanical characteristic may be lowered. In the present invention, it is assumed that the total sum of the volume contents of the resin, the discontinuous reinforced fibers and the voids constituting the resin sheet is 100% by volume.

An adhesive layer may be included in the boundary between the skin material and the resin sheet according to the embodiment of the present invention in order to enhance the strength of the imaging table for the mammography apparatus. In an example, the adhesive layer is formed by use of an adhesive agent after the skin material and the resin sheet are produced individually. However, in terms of productivity, the adhesive layer is preferably formed during molding. Examples which can be shown as a method for forming the adhesive layer during molding include the following methods. In the case where the resin kind of the matrix resin in the skin material is the same as the resin kind of the resin sheet, the resins of the two can flow during molding to form the adhesive layer. In the case where the resin kind of the skin material is different from the resin kind of the resin sheet, a base material to form the adhesive layer can be inserted therebetween to form the adhesive layer. The base material forming the adhesive layer in such a manner can be selected desirably from the resin kind of the skin material and the resin kind of the resin sheet. Examples of forms thereof include a thin sheet base material such as a nonwoven fabric. For example, in the case where the matrix resin of the skin material is an epoxy resin and the resin sheet is a polypropylene resin, a nonwoven fabric base material having a lower melting point than that of the polypropylene resin forming the resin sheet is inserted between the skin material and the resin sheet. Due to such a configuration, the nonwoven fabric forms an anchoring structure together with the epoxy resin while a part of polypropylene resin derived from the nonwoven fabric is melted and bonded with the polypropylene resin of the resin sheet. Thus, the adhesive layer can be formed with high strength.

The resin sheet according to the embodiment of the present invention is preferably a foam material. In the case where a foam material including voids is used, the weight in the thickness direction is reduced to improve the X-ray transparency. More preferably, the foam material according to the embodiment of the present invention is a foam material constituted by closed cells. The closed cells designate a state in which bubbles present inside the material are not linked with one another but partitioned by walls. Since the bubbles are not linked with one another, the matrix resin of the skin material can be inhibited from permeating the voids of the foam material during molding, so as to suitably reduce a variation in X-ray transparency property acquired at any point.

Each foam cell of the closed cells belonging to the foam material according to the embodiment of the present invention preferably has a ratio (minor diameter/major diameter) of the minor diameter to the major diameter of 0.25 to 0.90, in order to improve the compactness of the closed cells to obtain an excellent mammography image. The (minor diameter/major diameter) expressed as the ratio between the major diameter and the minor diameter is more preferably 0.30 to 0.80 and even more preferably 0.35 to 0.75. Any ones of the aforementioned upper and lower limits may be combined as a range. In the (minor diameter/major diameter) expressed as the ratio between the major diameter and the minor diameter, the average minor diameter of the foam cells of the closed cells is preferably 25 µm to 250 µm, more preferably 25 µm to 225 µm, and even more preferably 50 µm to 200 µm. Any ones of the aforementioned upper and lower limits may be combined as a range. This is preferable because, due to such a range, the matrix resin contained in the skin material can be inhibited from permeating the foam material while the surface irregularities formed due to shortage of the matrix resin in the skin material caused by the penetration of the matrix resin from the skin material to the foam material can be inhibited. If the average minor diameter is long, the intervals of the walls forming the closed cells are so long that there is a fear that it is difficult to inhibit the permeation of the matrix resin.

Here, the ratio between the major diameter and the minor diameter is defined as a value obtained by dividing the minor diameter of each closed cell by the major diameter thereof. A desired section in a region including the foam material in the imaging table for the mammography apparatus is observed to measure the major diameter and the minor diameter of each closed cell, and the minor diameter is divided by the major diameter in the same closed cell to calculate a ratio. An average value of the ratios obtained thus is used. More specifically, a small piece is arbitrarily cut out from a region of a flat face portion in the X-ray irradiation surface of the imaging table for the mammography apparatus. The small piece is embedded in epoxy resin and a section thereof in the thickness direction of the X-ray irradiation surface is polished to produce a sample. The sample is observed at a magnification of 100 times by use of a laser microscope, so as to measure the major diameter and the minor diameter of each of 50 closed cells observed within an observed image. An average value thereof is calculated and acquired.

The minor axis of each closed cell is preferably substantially parallel with the thickness direction of the imaging table. Such a configuration is preferable because a homogenous cell structure in which the minor axes of the cells are set up in the thickness direction. Thus, a variation in weight distribution in the thickness direction at any point of the X-ray irradiation surface is reduced so that unevenness in the taken image can be reduced. Incidentally, "substantially parallel" designates that the angle with respect to the axis of the thickness direction is within ±30°. The angle with respect to the axis of the thickness direction is acquired by use of a laser microscope in the same manner as the ratio (minor diameter/major diameter) between the major diameter and the minor diameter of the closed cells. That is, the inclination of the minor axis with respect to the axis of the thickness direction is measured for each of 50 closed cells selected desirably from closed cells observed within an observed image, and an average value thereof is calculated.

<Configuration>

The imaging table for the mammography apparatus according to the embodiment of the present invention typically has a mechanism to be supported in a cantilever state on the mammography apparatus. A coupling member which can be connected to a body of the mammography apparatus is preferably provided in a region which is formed by the carbon fiber composite material. Alternatively, the coupling member which can be connected to the body of the mammography apparatus is provided in a region formed by the planar body. That is, a part to which the coupling member can be attached is provided in the aforementioned region, and the coupling member is attached to the part. Due to such a configuration, the imaging table is coupled with the body of the mammography apparatus through the carbon fiber composite material portion high in rigidity so that a major part of a load serving during imaging can be taken charge of by the carbon fiber composite material. Thus, deflection during the imaging can be inhibited so that unevenness in a taken image can be prevented.

The coupling member may be supported in both the aforementioned region and another region formed by another material.

The position where the coupling member is attached is not particularly limited as long as it is within the region formed by the carbon fiber composite material or within the region of the planar body. The coupling member is preferably attached on an inner wall of the carbon fiber composite material or an inner of the planar body, in terms of designability of the imaging table for the mammography apparatus obtained therefrom. More preferably, the coupling member is attached to each inner wall of two side faces in a surface having an opening portion which will be described later.

In the case where the coupling members are attached to the side faces, the X-ray irradiation surface can be expanded so that even a position close to a body of an examinee subjected to mammography can be imaged. Thus, an area which can be examined can be expanded.

Examples of a structure for connecting the body of the mammography apparatus and the imaging table include a method in which the imaging table provided with a coupling member is connected through the coupling member to a frame provided in the body of the mammography apparatus, and a method in which the imaging table for the mammography apparatus has a frame-like coupling member, and the coupling member is fixed to the mammography apparatus, thereby connecting the imaging table thereto.

The imaging table for the mammography apparatus according to the embodiment of the present invention preferably has a first member for forming the X-ray irradiation surface, and a second member for forming a bottom surface opposed to the X-ray irradiation surface. In the present invention, the unidirectional carbon fiber composite material or the resin sheet is used. Accordingly, it can be considered that there is a problem that the material cannot follow a shape in molding, and it is difficult to mold a complicated shape such as a hollow box-like shape. However, in the case where a method for molding members constituting the imaging table separately is used, the number of curved faces or corner portions in the individual members can be reduced so that the imaging table can be manufactured with good productivity. The imaging table according to the embodiment of the present invention may include third and fourth members separately.

The material of the second member may be the same as the material of the first member, or may be formed by only the carbon fiber woven fabric composite material. The second member is preferably formed by at least one kind selected from the group consisting of metal, plastic and elastomer.

In the case where such a material is used for the second member, the function of securing X-ray transparency and the function of imparting a shape such as a handle for an examinee can be separated. Thus, a complicated shape can be suitably designed with good productivity while the functions required as a mammography apparatus in the related art are maintained.

From the viewpoint of processability and dimensional accuracy, metal is preferably used as the material of the second member. Examples of kinds of such metals include aluminum, copper, nickel, tin, iron, magnesium, chrome, tungsten, zinc, lead, and alloys of those metals. In addition, the second member may be composed of one kind of metal material, or two or more kinds of metals may be combined.

Plastic is preferably used as the material of the second member in terms of moldability/processability and manufacturing cost. Either a thermosetting resin or a thermoplastic resin may be used. Examples of the thermosetting resin include epoxy resin, vinyl ester resin, phenolic resin, polyurethane resin, urea resin, melamine resin, etc. Examples of the thermoplastic resin include polypropylene resin, polyethylene resin, polycarbonate resin, polyamide resin, polyester resin, polyarylene sulfide resin, and polyphenylene sulfide resin. In addition, a cyclic oligomer which is a precursor of any one of those resins is also used preferably. In addition, the plastic as the material of the second member may contain a filler such as glass fibers in order to enhance the mechanical characteristic.

Alternatively, an elastomer may be used as the material of the second member in order to protect an examinee. Examples of the elastomer include silicone rubber, urethane rubber, thermoplastic elastomer, etc.

The shape of the first member is not particularly limited as long as it includes the X-ray irradiation surface. The shape of the first member preferably includes the top surface including the X-ray irradiation surface. A shape including a standing wall portion in the outer circumference of the top surface including the X-ray irradiation surface is also preferred. In the case where the first member includes the standing wall portion, deformation caused by a load received from the pressing plate 3 during imaging by mammography can be inhibited. On the other hand, the shape of the second member is, for example, a shape suitable for constituting the other region than the region constituted by the first member in the imaging table for the mammography apparatus. The second member preferably has a shape including a bottom surface opposed to the X-ray irradiation surface, and a standing wall portion erectly provided in the outer circumference of the bottom surface.

The imaging table preferably includes the first member forming the top surface including the X-ray irradiation surface, and the second member forming the bottom surface opposed to the X-ray irradiation surface, and the standing wall portion erectly provided in the outer circumference of the bottom surface.

The height of the standing wall in the first member is preferably 10 mm or higher. In the case where the height of the standing wall is 10 mm or higher in the first member, it is possible to secure a large space where an X-ray detector can be received. The height of the standing wall is a distance between the upper portion of the top surface and an end portion of the standing wall in a direction perpendicular to the top surface. Further, the height of the standing wall is more preferably 20 mm or higher, and particularly preferably 30 mm or higher.

The imaging table for the mammography apparatus according to the embodiment of the present invention preferably has a structure in which the imaging table for the mammography apparatus according to the embodiment of the invention has a connection surface to be connected to the body of the mammography apparatus, and an opening portion is provided in the connection surface.

Figure 2:
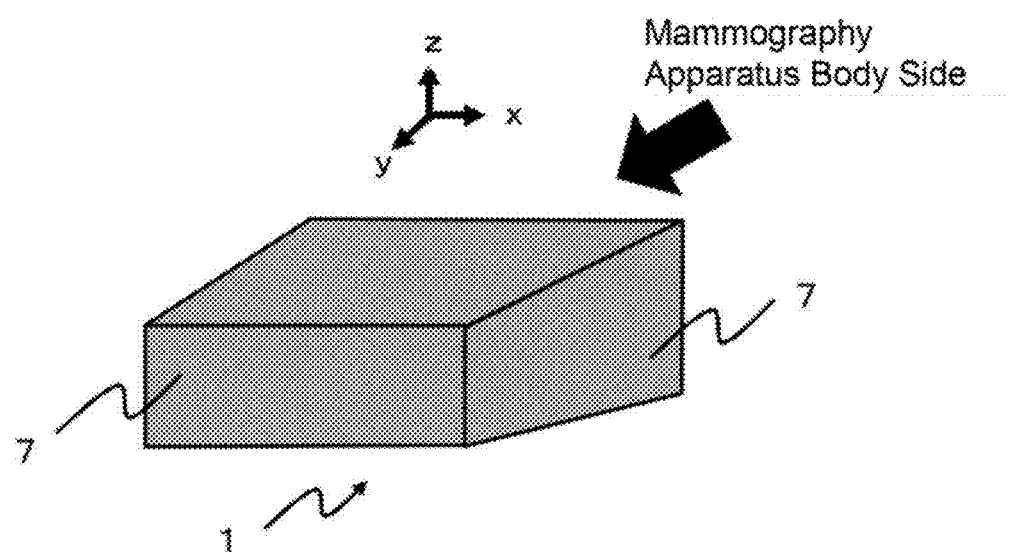
FIG. 2 is a schematic view showing an example of the external appearance of an imaging table for the mammography apparatus according to the embodiment of the present invention.
Figure 3A:
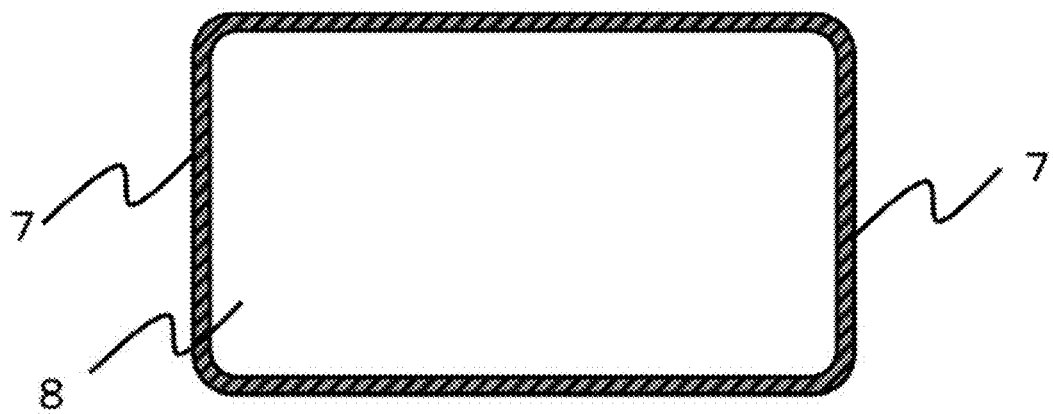
FIG. 3a is a schematic view showing an example of an opening portion of the imaging table for the mammography apparatus according to the embodiment of the present invention.
Figure 3B:
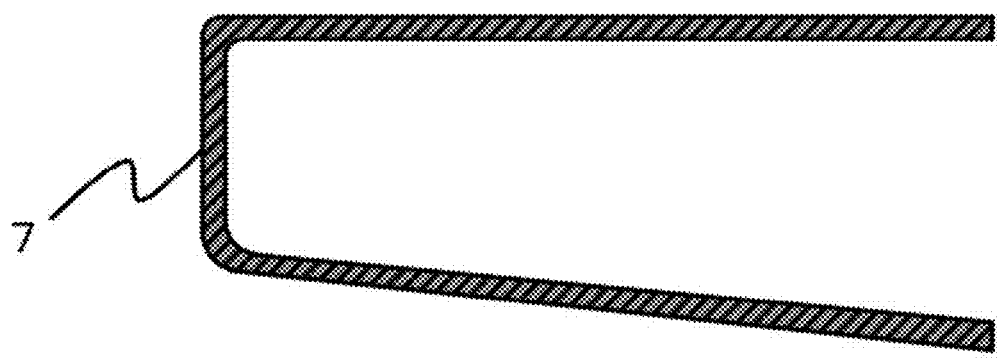
FIG. 3b is a sectional view showing an example of a sectional shape taken on y-z plane in FIG. 2.
Figure 3C:
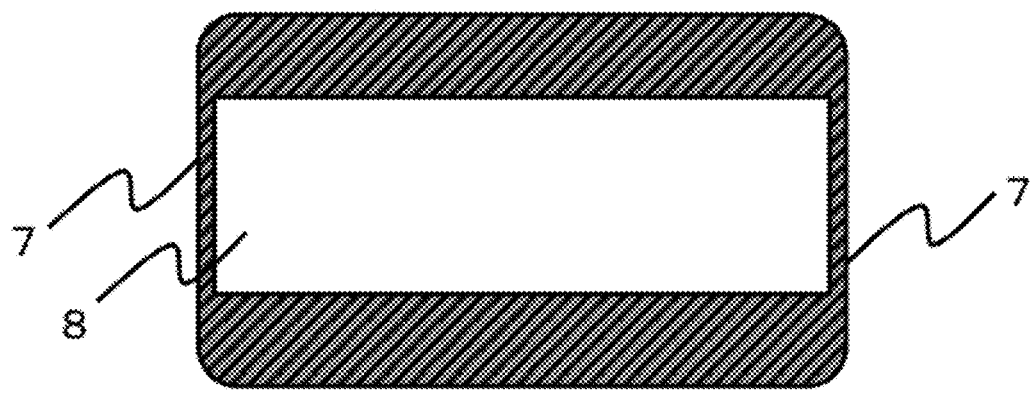
FIG. 3c is a schematic view showing an example of the opening portion of the imaging table for the mammography apparatus according to the embodiment of the present invention.
Figure 3D:
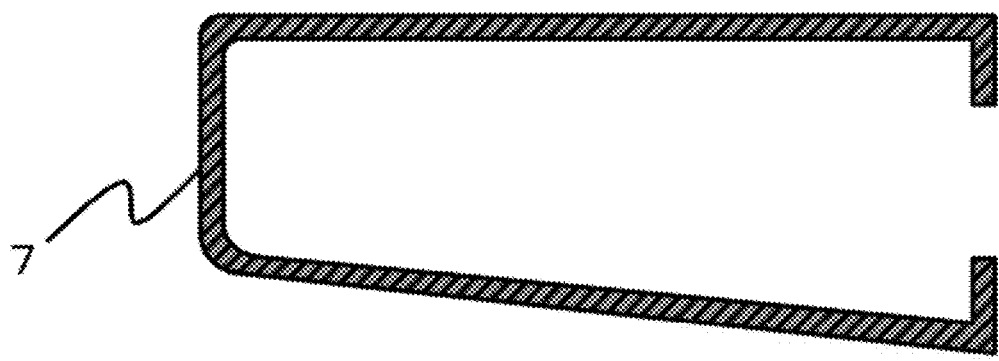
FIG. 3d is a sectional view showing an example of the sectional shape taken on y-z plane in FIG. 2.

The mammography apparatus imaging table 1 shown in FIG. 2 has standing wall portions 7, and an opening portion is provided in the connection surface (on the mammography apparatus body side) to be connected to the body of the mammography apparatus. As shown in FIG. 3*a* and FIG. 3*b*, the opening portion 8 may be opened all over the connection surface to be connected to the body of the mammography apparatus. Alternatively, as shown in FIG. 3*c* and FIG. 3*d*, the opening portion 8 may be opened in a part of the connection surface. FIG. 3*b* and FIG. 3*d* are sectional views each showing an example of a sectional shape taken on y-z plane in the mammography apparatus imaging table 1 shown in FIG. 2.

Due to the opening portion 8 provided in the mammography apparatus imaging table 1, the mammography apparatus imaging table 1 can be detached from and attached to the body of the mammography apparatus easily. Thus, maintenance can be performed easily. In addition, the aforementioned coupling members are preferably bonded to the two standing wall portions 7 opposed to each other in the surface including the opening portion 8, respectively.

A third member bonded to both the standing wall portion of the first member and the standing wall portion of the second member is preferably provided. The bonding position of the third member may be on the inner wall side of the surface an examinee will touch, by way of example (FIG. 17). Due to such a configuration, the third member can serve as a reinforcing member, thereby improving the rigidity. Thus, opening can be inhibited from occurring at an end portion of the standing wall portion of the first member and an end portion of the standing wall portion of the second member so that the positional accuracy during imaging can be improved.

Figure 22A:
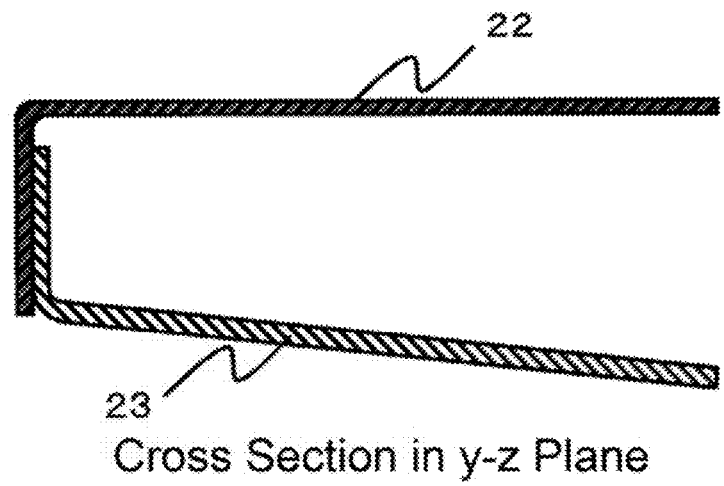
FIG. 22*a* is a sectional view showing an example of the sectional shape taken on y-z plane in FIG. 19*a*.
Figure 22B:
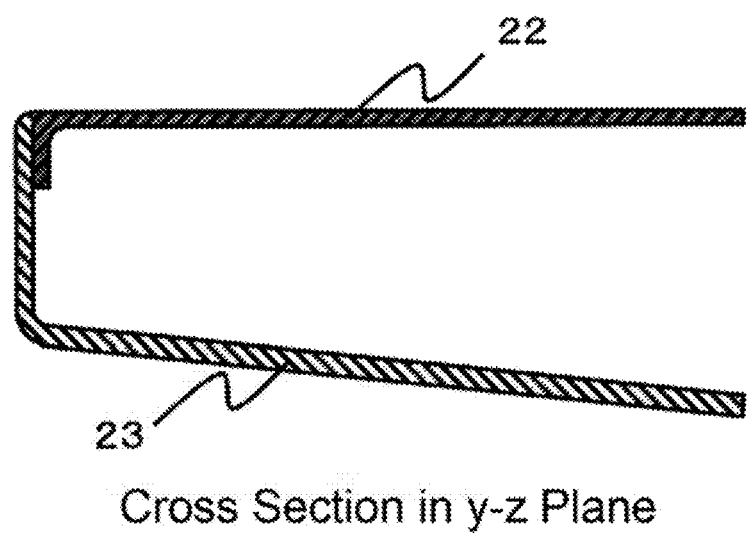
FIG. 22*b* is a sectional view showing an example of the sectional shape taken on y-z plane in FIG. 19*a*.

Preferably, no border line exists between the first member and the second member in an opposed surface to the connection surface to the apparatus. The opposed surface is a surface an examinee will touch. Due to such a configuration, there is no irregularity in the region the bare skin of the examinee will touch during imaging. It is therefore possible to relax the feeling of discomfort given to the examinee during imaging. The configuration is not particularly limited as long as no border line exists between the first member and the second member in the opposed surface to the connection surface to the apparatus. Examples of the configuration include a configuration (FIG. 22a) in which the length of the standing wall located in the opposed surface to the connection surface to the apparatus in the first member is extended to the height of the standing wall of the second member so that the standing walls can be bonded to cover the standing wall of the second member with the standing wall of the first member, and a configuration (FIG. 22b) in which the length of the standing wall located in the opposed surface to the connection surface to the apparatus in the second member is extended to the height of the standing wall of the first member so that the standing walls can be bonded to cover the standing wall of the first member with the standing wall of the second member.

A method for manufacturing the imaging table for the mammography apparatus according to the embodiment of the present invention preferably includes the following steps (I) and (II).

Step (I): a step of imparting a shape of a single-surface mold to a base material containing carbon fibers (A) including continuous fibers, and a thermosetting resin (B).

Step (II): a step of covering a space including the single-surface mold and the base material with a flexible film, and applying heat and pressure thereto.

In the case where such a manufacturing method is used, a shape such as a curved face can be imparted easily while voids can be reduced. Thus, the imaging table for the mammography apparatus can be obtained with high dimensional accuracy suitably.

The step (I) is a step in which a prepreg is disposed in a single-surface mold as a base material including the carbon fibers (A) including continuous fibers and the thermosetting resin (B). The thermosetting resin (B) in the prepreg must be bonded in pressed manner to another prepreg or a surface of the mold when the prepreg is laminated. Thus, the prepreg is preferably in a semi-cured state excellent in tackiness. Among the thermosetting resins, the epoxy resin is preferred in consideration of the tackiness in a pasting step and the mechanical characteristic as a molded product obtained therefrom. Examples of a method for disposing the prepreg include a method in which the surface shape of the single-surface mold is imparted to layers of the prepreg one by one, and a method in which the surface shape of the single-surface mold is imparted to a laminate in which two or more layers have been deposited, together. In addition, a resin sheet may be further inserted between one prepreg and another prepreg.

Figure 9:
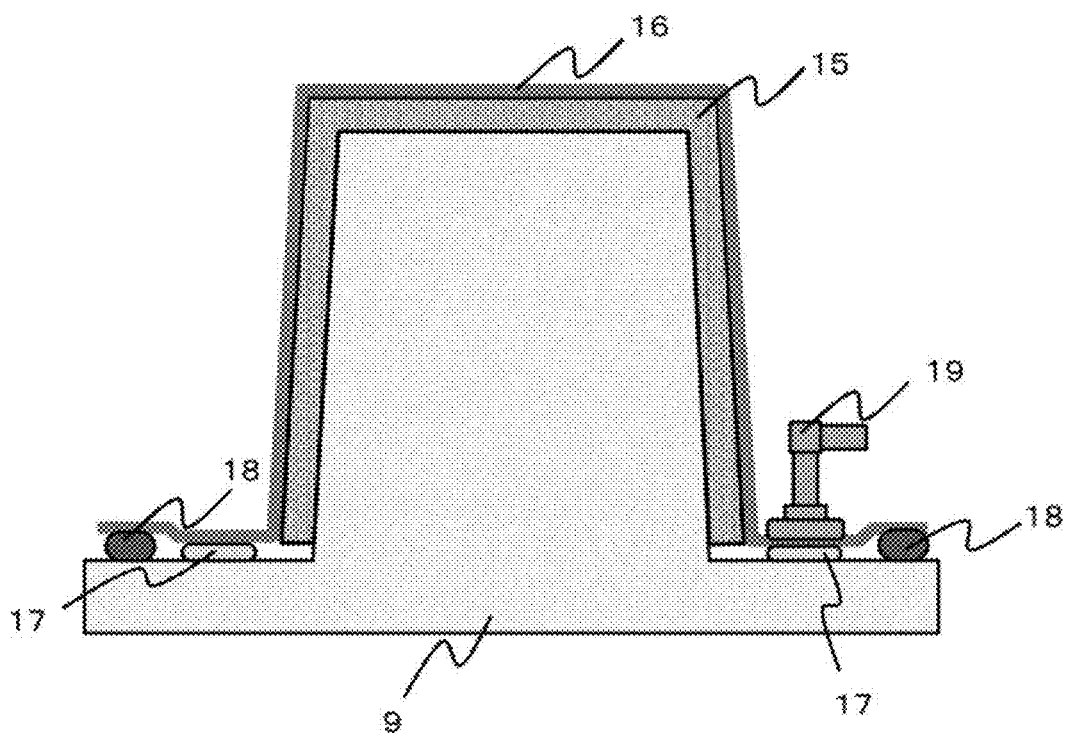
FIG. 9 is a schematic view showing an example of a part of a step (II) of the method for manufacturing the imaging table for the mammography apparatus according to the embodiment of the present invention.

The step (II) is a step in which the region including the single-surface mold and the prepreg are covered with a flexible film 16, and heat and pressure are applied thereto in a state where the pressure in the space formed by the single-surface mold 9 and the flexible film 16 is reduced (FIG. 9). For example, there is a method in which an end portion of the flexible film 16 larger than the prepreg which has been shaped is brought into close contact with the single-surface mold 9 by use of a seal material 18. In this method, a valve 19 serving as a suction opening is placed in a part of the close contact surface between the flexible film 16 and the single-surface mold 9 so that the air existing in a molding space (a space formed by the single-surface mold and the flexible film) is sucked through the suction opening by use of a vacuum pump, thereby reducing the pressure in the molding space. At that time, the pressure in the molding space is lower than that in the outside so that the shaped prepreg itself is pressurized. In addition, preferably at that time, another mold having a shape corresponding to the single-surface mold is pressed in order to form a well-designed surface.

Examples of a method for pressing the aforementioned mold include a method in which after the step (I) where the prepreg is deposited on the single-surface mold, the aforementioned mold is pressed against the surface of the prepreg so as to be brought into close contact therewith, and the mold is then entirely covered with the flexible film, and a method in which a region including the single-surface mold and the prepreg are covered with the flexible film, the pressure in the space formed by the single-surface mold and the flexible film is reduced, and the aforementioned mold is then pressed onto the flexible film from above. After that, the prepreg and the single-surface mold are thrown into an autoclave, a hot air oven or the like to be heated. Thus, curing reaction of the thermosetting resin (B) proceeds so that an imaging table for a mammography apparatus can be obtained. By use of such a molding method, the gas existing in the molding space is sucked to reduce the pressure therein so that the air or the like among the shaped layers of the prepreg or between the prepreg and the surface of the single-surface mold can be also eliminated to inhibit formation of voids in the imaging table for the mammography apparatus obtained therefrom. Thus, there is an effect of providing a good mechanical characteristic and a good surface quality. Further, heating and pressurizing are preferably performed by the autoclave because the formation of voids can be further reduced.

More preferably in the step (I), the shape of the single-surface mold is imparted to a base material by an automatic lamination apparatus.

Typically, the unidirectional carbon fiber composite material requires a step of cutting a large-sized base material into a complicated shape in advance in order to form a shape without any wrinkle. On the other hand, in the case where a shape of a single-surface mold is imparted to a narrow base material by an automatic lamination apparatus, the shape can be formed without a cutting step. In addition, due to the automation used fully, human errors can be reduced so that a variation in quality among samples can be also reduced suitably.

EXAMPLES

Examples will be shown below for further specific description of the present invention. Description will be made in the following text using signs in which alphabets are often attached to signs written on the drawings for the sake of discrimination. However, those alphabets are not shown on the drawings.

[Unidirectional Carbon Fiber Prepreg]

"TORAYCA® PREPREG" P3252S-10 made by TORAY Industries, Inc. was prepared as a unidirectional carbon fiber prepreg.

[Carbon Fiber Woven Fabric Prepreg]

"TORAYCA® PREPREG" F6347B-05P made by TORAY Industries, Inc. was prepared as a carbon fiber woven fabric prepreg.

[Calculation of Specific Bending Elastic Modulus]

Using a test piece cut out and obtained from a flat face portion of an X-ray irradiation surface of a manufactured imaging table for a mammography apparatus, a three-point bending elastic modulus Eb was acquired according to JIS K7074 (1988). In addition, density p was acquired according to JIS Z8807 (2012) before the examination of the elastic modulus Eb. A specific bending elastic modulus was calculated from the obtained bending elastic modulus Eb and the obtained density p by use of the following equation:

(specific bending elastic modulus)=(bending elastic modulus:Eb $[GPa])^{1/3}$×(density: $\rho$ $[g/cm^3])^{-1}$

[Measurement of Aluminum Equivalent]

At each of a total of 10 places set desirably within the flat face portion of the X-ray irradiation surface of the manufactured imaging table for the mammography apparatus, the dose of X-rays transmitted by the flat face portion was measured by a dosimeter. The X-rays were made incident on the flat face portion in a direction perpendicular to the thickness at X-ray irradiation tube voltages of 60 kV and 20 kV by use of an X-ray irradiation device. Then, an aluminum equivalent was calculated from the obtained transmitted X-ray dose. An X-ray high voltage device for diagnosis KXO-30F made by TOSHIBA Corporation was used as the X-ray irradiation device, and a radiation monitor Model No. 2025 made by Radiation Corporation was used as the dosimeter.

The aluminum-equivalent X-ray transparency dose in the X-ray irradiation surface of the flat face portion is preferably 0.5 mmAL or lower at any point in any condition of an X-ray irradiation tube voltage, or may be 0.5 mmAL or lower in any condition of the X-ray irradiation tube voltage within a range of 20 kV to 60 kV, or may be 0.5 mmAL or lower at the X-ray irradiation tube voltage of 20 kV or 60 kV.

[Measurement of Ratio (Minor Diameter/Major Diameter) between Major Diameter and Minor Diameter of Closed Cell]

A small piece was desirably cut out from a region of a flat face portion of the X-ray irradiation surface of the manufactured imaging table for the mammography apparatus. The small piece was embedded in epoxy resin and a section thereof in the thickness direction of the X-ray irradiation surface was polished to produce a sample. The sample was observed at a magnification of 100 times by use of a laser microscope (VK-9500 made by Keyence Corporation), so as to measure the major diameter and the minor diameter of each of 50 closed cells observed within an observed image. An average value thereof was calculated and acquired.

[Measurement of Angle between Minor Axis and Thickness-Direction Axis]

In the same manner as in the measurement of the ratio (minor diameter/major diameter) between the major diameter and the minor diameter of the closed cells, the sample was observed at a magnification of 100 times by use of the laser microscope (VK-9500 made by Keyence Corporation), so as to measure the inclination of the minor axis with respect to the thickness-direction axis in each of 50 closed cells selected at random from closed cells observed within an observed image. An average value thereof was calculated and acquired.

Example 1

Figure 4:
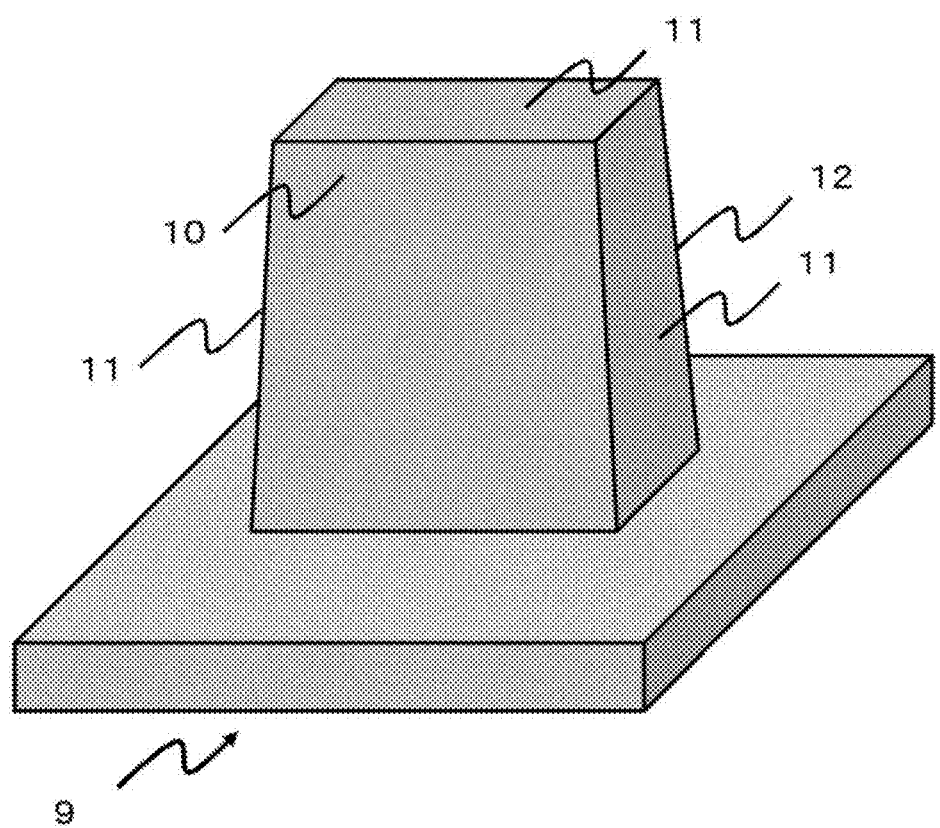
FIG. 4 is a schematic view showing an example of a single-surface mold for molding the imaging table for the mammography apparatus according to the embodiment of the present invention.

On a single-surface mold 9 shown in FIG. 4, 12 layers of a unidirectional carbon fiber prepreg 13 were deposited. The single-surface mold 9 includes a surface A 10 for forming a top surface including an X-ray irradiation surface, three surfaces (B 11) for forming standing wall surfaces in side surfaces of a mammography apparatus imaging table 1A, and a surface C 12 for forming a bottom surface of the mammography apparatus imaging table 1A. A step of imparting the shape of the single-surface mold 9 to the unidirectional carbon fiber prepreg 13 was carried out by a method in which the layers of the unidirectional carbon fiber prepreg 13 were deposited on the aforementioned surfaces of the single-surface mold 9 one by one.

Figure 5:
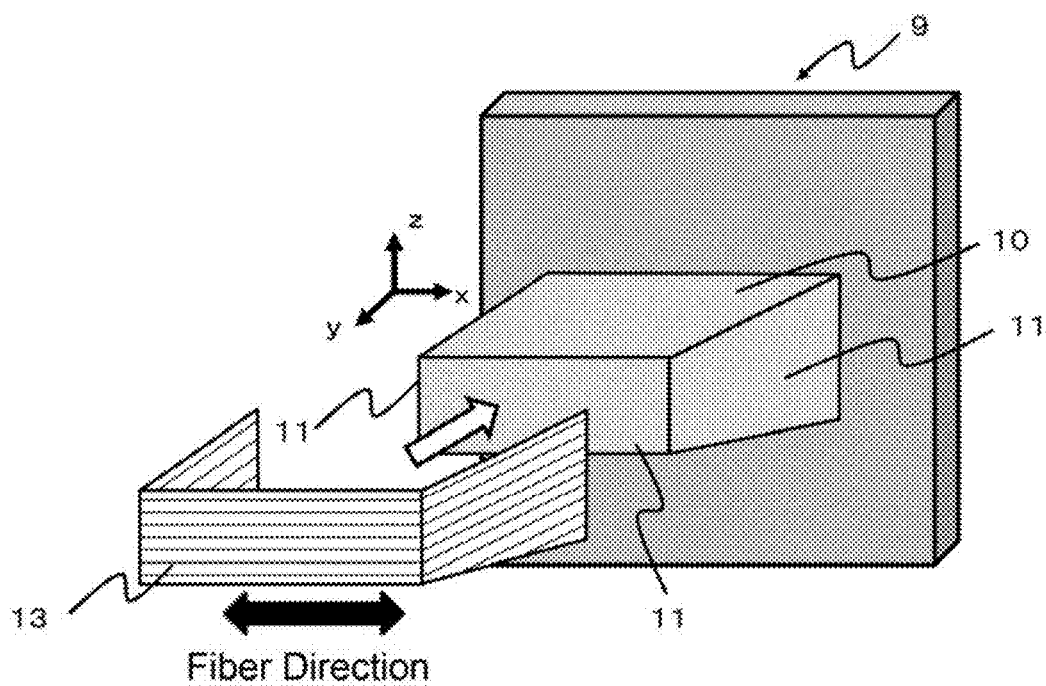
FIG. 5 is a schematic view showing an example of a part of a step (I) of a method for manufacturing the imaging table for the mammography apparatus according to the embodiment of the present invention.
Figure 6:
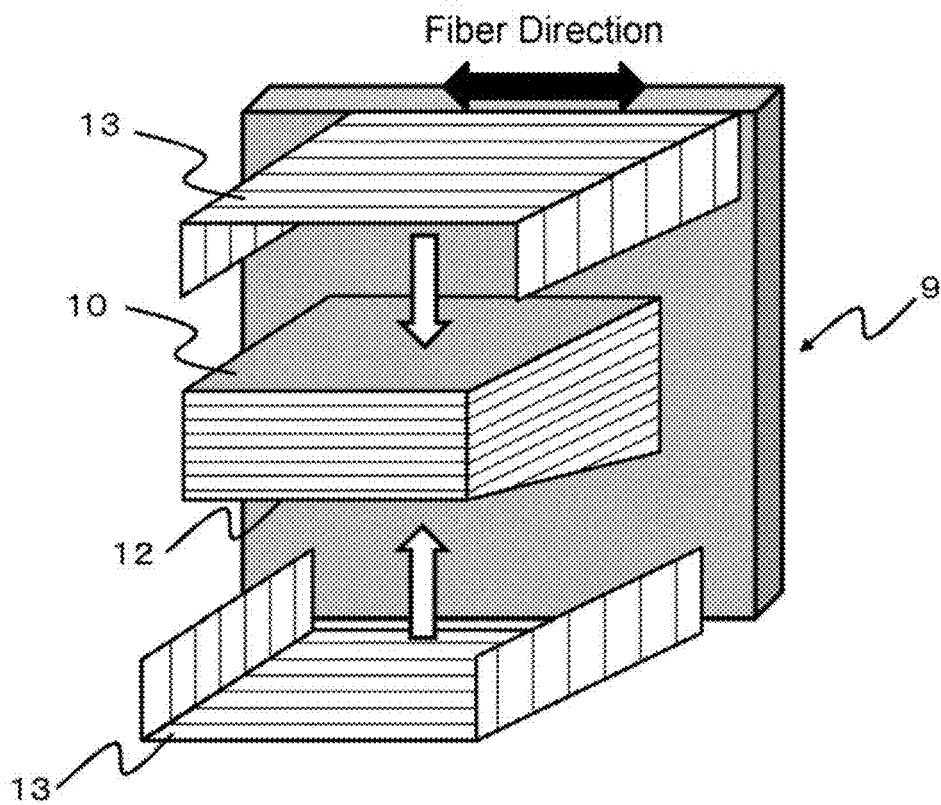
FIG. 6 is a schematic view showing an example of a part of the step (I) of the method for manufacturing the imaging table for the mammography apparatus according to the embodiment of the present invention.
Figure 7:
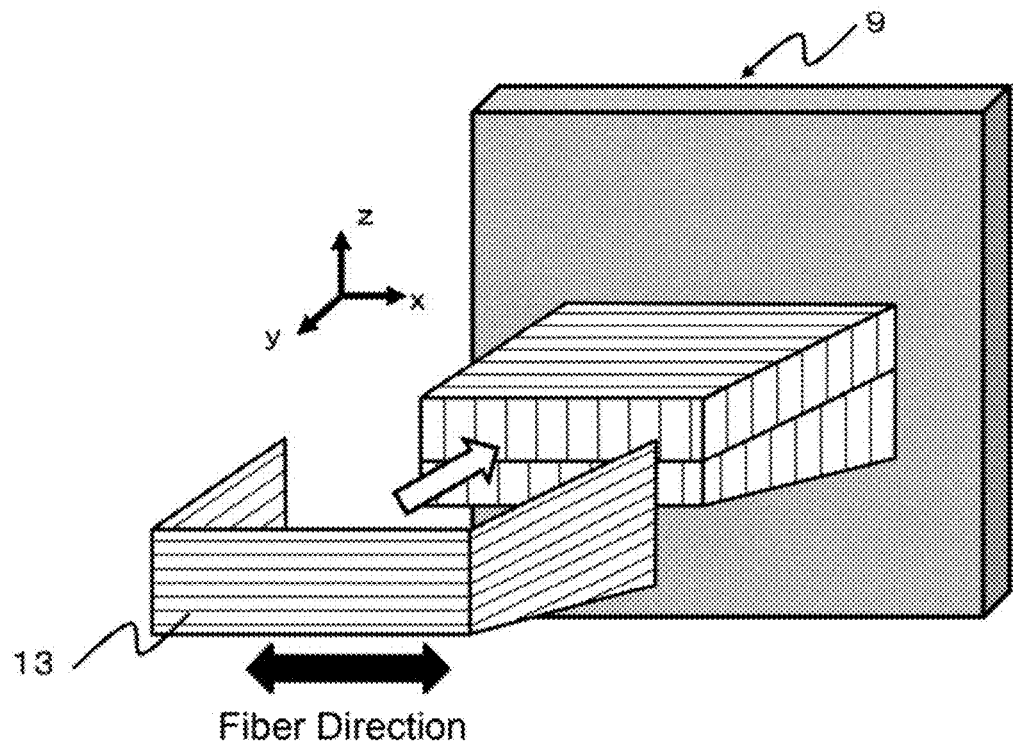
FIG. 7 is a schematic view showing an example of a part of the step (I) of the method for manufacturing the imaging table for the mammography apparatus according to the embodiment of the present invention.

First, the unidirectional carbon fiber prepreg 13 was deposited on the surfaces B 11 (FIG. 5). After that, the unidirectional carbon fiber prepreg 13 was deposited on the surface A 10 and the surface C 12 with a lamination configuration $[0/90]_{3S}$ (FIG. 6). Finally, the unidirectional carbon fiber prepreg 13 was deposited on the surfaces B 11 (FIG. 7).

In the aforementioned lamination configuration, the x-direction shown in FIG. 5 coincides with a direction of 0°.

Here, [0/90] designates a lamination of two layers in which fiber orientation directions of the unidirectional carbon fiber prepreg 13 were a direction of 0° and a direction of 90° respectively. In addition, the subscript sign 3S designates that the aforementioned lamination of two layers was repeated three times, and the lamination was further performed symmetrically. Accordingly, a total of 12 layers of the unidirectional carbon fiber prepreg 13 were laminated.

In the lamination configuration, the unidirectional carbon fiber prepreg 13 was cut by three kinds of cutting patterns, that is, a cutting pattern to be laminated on the surfaces B 11, a 0°-direction cutting pattern (with carbon fibers oriented in the x-direction) to be laminated on the surfaces A 10 and C 12, and a 90°-direction cutting pattern (with carbon fibers oriented in the y-direction) to be laminated on the surfaces A 10 and C 12.

The outer circumference of the region where the unidirectional carbon fiber prepreg 13 had been deposited was covered with a seal material 18 (bringing a flexible film 16 into close contact with the mold, thereby tightly closing the mold). After that, a bleeder 17 (playing a role of a spacer serving as an air passage) made of a thick nonwoven fabric was disposed on an outer circumferential portion of a prepreg laminate 15 as shown in FIG. 9.

A valve 19 provided with a check valve was disposed as a suction opening on the bleeder 17. After that, the single-surface mold was covered with the flexible film 16, and the seal material 18 and the flexible film 16 were brought into close contact with each other. After that, a vacuum pump was connected to the valve 19 serving as a suction opening so as to suck the air from a molding space (a space formed by the single-surface mold and the flexible film 16 and including the region where the unidirectional carbon fiber prepreg 13 had been deposited), thereby reducing the pressure in the molding space. After that, the single-surface mold was thrown into an autoclave apparatus. The temperature of the single-surface mold was increased at a rate of 2.5° C./min under the condition of 3 atm. After the temperature reached 130° C., the single-surface mold was retained for 90 minutes. By heating and pressurizing the single-surface mold in this manner, the thermosetting resin composition in the prepreg 13 was cured. After molding, a molded product was released from the single-surface mold 9. End faces of the molded product were trimmed by a numerical control (NC) router to obtain a mammography apparatus imaging table 1A.

Figure 8A:
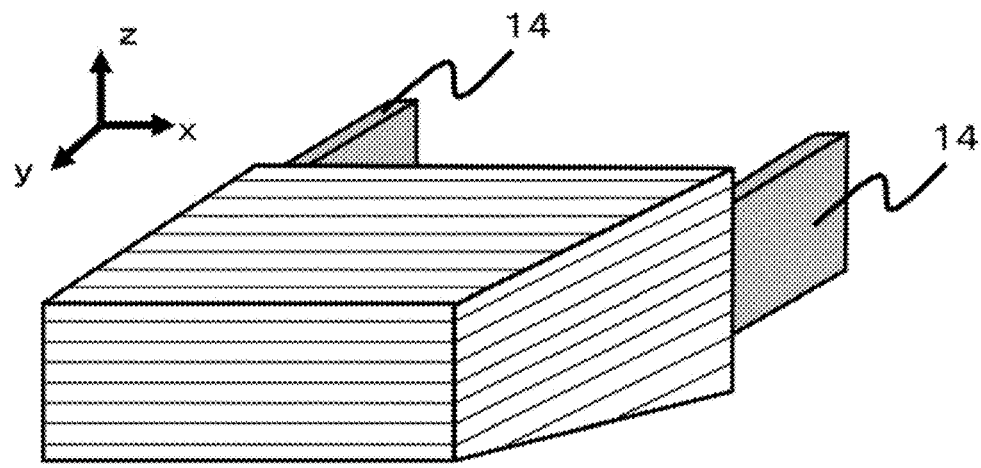
FIG. 8*a* is a schematic view showing an example the external appearance of the imaging table for the mammography apparatus according to the embodiment of the present invention.
Figure 8B:
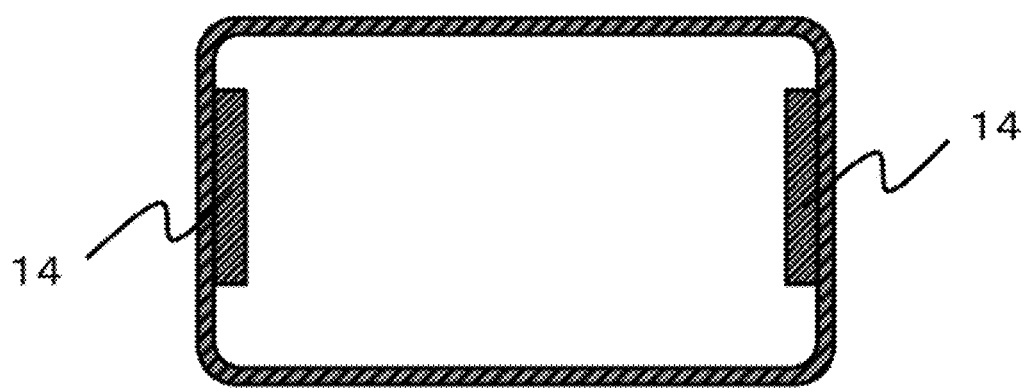
FIG. 8*b* is a sectional view showing an example of a sectional shape taken on x-z plane in FIG. 8*a*.

The obtained mammography apparatus imaging table 1A (FIG. 8a, FIG. 8b and FIG. 8c) had an opening portion 8. Coupling members 14 made of an aluminum alloy were inserted through the opening portion, and bonded to inner wall surfaces of two standing wall portions opposed to each other so as to form the opening portion, respectively, by use of a two-liquid epoxy adhesive agent (FIG. 8a and FIG. 8b). The mammography apparatus imaging table 1A was assembled to a mammography apparatus body 2, and a mammography image was taken. The obtained image was good in quality. In addition, according to the method described in the aforementioned [Measurement of Aluminum Equivalent], the aluminum equivalent X-ray transparency dose (aluminum equivalent) of the surface A (X-ray irradiation surface 5) was measured. As a result, the aluminum equivalent was 0.17 mmAL on the condition of the X-ray irradiation tube voltage of 60 kV, and 0.14 mmAL on the condition of 20 kV. In addition, a rectangular test piece was cut out by use of a numerical control (NC) router so that the x-direction in the obtained mammography apparatus imaging table 1A was set as the longitudinal direction. The specific bending elastic modulus calculated by the method described in [Calculation of Specific Bending Elastic Modulus] was 2.70. In addition, the thickness of the surface A (X-ray irradiation surface 5) of the obtained mammography apparatus imaging table 1A was 1.28 mm.

Example 2

Figure 8C:
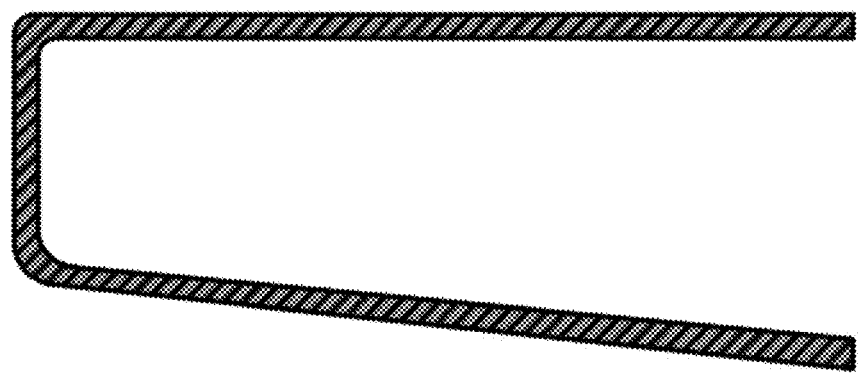
FIG. 8*c* is a sectional view showing an example of a sectional shape taken on y-z plane in FIG. 8*a*.

By use of the same single-surface mold as in (Example 1), a mammography apparatus imaging table 1B was obtained in the same method as in (Example 1), except that the unidirectional carbon fiber prepreg 13 was laminated with a lamination configuration [0/90/0/90/0/0/90/0/90/0] from the surface side of the mold, and one layer of a carbon fiber woven fabric prepreg was laminated on the outermost layers of all the surfaces A 10, B 11 and C 12. The obtained mammography apparatus imaging table 1B had an opening portion 8. Further, coupling members 14 made of an aluminum alloy were bonded in the same manner as in (Example 1) (FIG. 8a, FIG. 8b and FIG. 8c). The mammography apparatus imaging table 1B was assembled to a mammography apparatus body 2, and a mammography image was taken. The obtained image was good in quality. According to the method described in the aforementioned [Measurement of Aluminum Equivalent], the aluminum equivalent of the surface A (X-ray irradiation surface 5) was measured. As a result, the aluminum equivalent was 0.18 mmAL on the condition of the X-ray irradiation tube voltage of 60 kV, and 0.15 mmAL on the condition of 20 kV.

In addition, the specific bending elastic modulus of the obtained mammography apparatus imaging table 1B obtained in the same manner as in (Example 1) was 2.75. In addition, the thickness of the surface A (X-ray irradiation surface 5) of the obtained mammography apparatus imaging stand 1B was 1.30 mm.

Example 3

The unidirectional carbon fiber prepreg 13 was laminated with a lamination configuration [0/90]3s to obtain a prepreg laminate 15. The prepreg laminate 15 had a square shape, using one kind of cutting pattern for cutting the unidirectional carbon fiber prepreg 13. Therefore, waste such as end pieces was reduced. The laminate 15 was disposed in a pair of double-surface molds, that is, a female mold 20 and a male mold 21 shown in FIG. 10. The laminate 15 was heated and pressurized at a surface pressure of 1.0 MPa at 130° C. for 90 minutes by use of a hydraulic pressing machine to obtain a molded product.

Figure 11A:
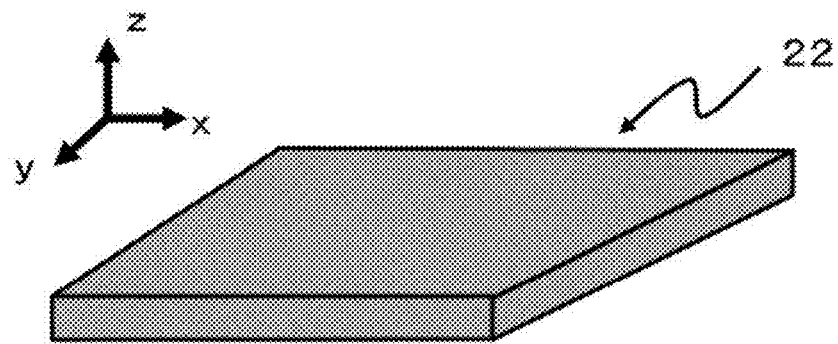
FIG. 11*a* is a schematic view showing an example of the external appearance of a first member constituting the imaging table for the mammography apparatus according to the embodiment of the present invention.
Figure 11B:
FIG. 11*b* is a sectional view showing an example of a sectional shape taken on y-z plane in FIG. 11*a*.

The surface pressure was calculated from an area (projected area viewed from the lamination direction) of the laminate before molding. In the molded product, standing wall surfaces were trimmed by a numerical control (NC) router so that the x-direction in FIG. 11a coincided with the direction of 0° to obtain a carbon fiber composite material member 22a (first member 22) which formed the surface A 10 and parts of the surfaces B 11 provided erectly on three sides in the outer circumference of the surface A 10 (FIG. 11a and FIG. 11b).

Figure 12A:
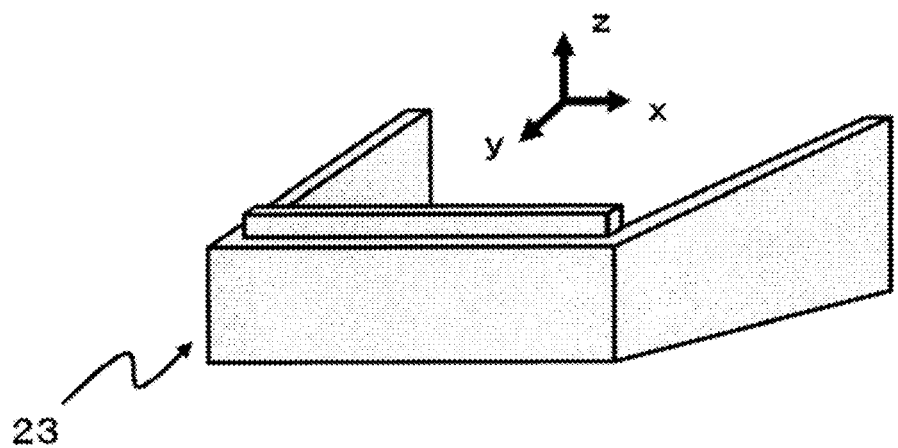
FIG. 12*a* is a schematic view showing an example of the external appearance of a second member constituting the imaging table for the mammography apparatus according to the embodiment of the present invention.
Figure 12B:
FIG. 12*b* is a sectional view showing an example of a sectional shape taken on y-z plane in FIG. 12*a*.
Figure 13A:
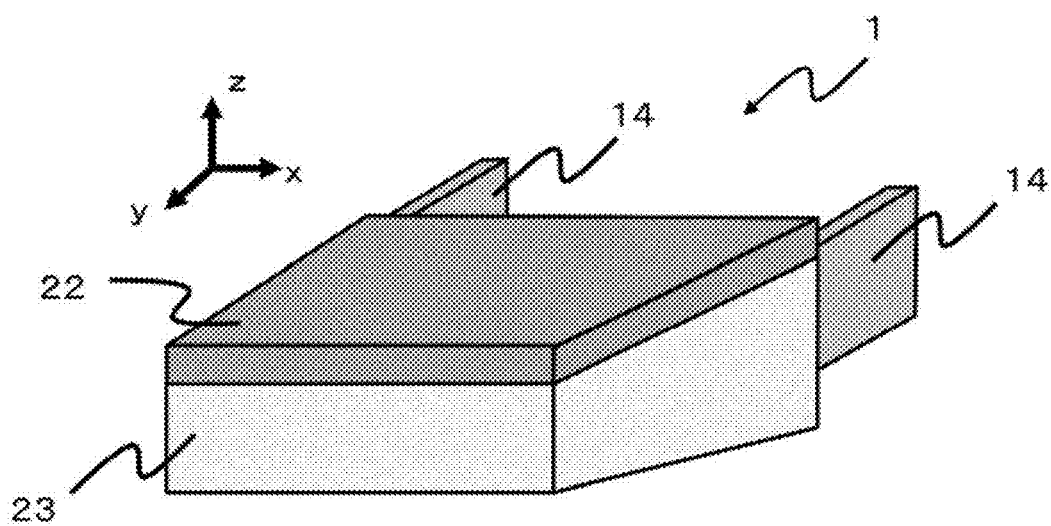
FIG. 13*a* is a schematic view showing an example of the external appearance of the imaging table for the mammography apparatus, the imaging stand including the first member in FIG. 11*a* and the second member in FIG. 12*a*.
Figure 13B:
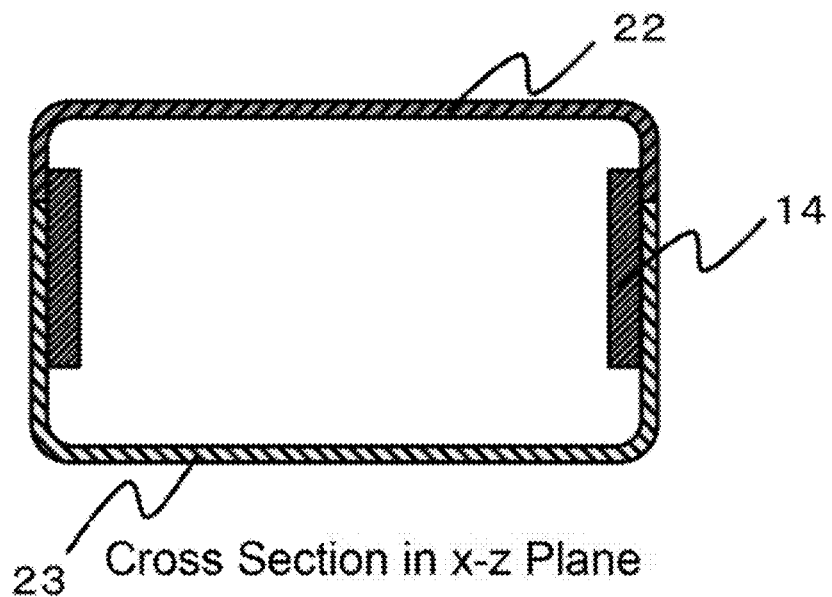
FIG. 13*b* is a sectional view showing an example of a sectional shape taken on x-z plane in FIG. 13*a*.
Figure 13C:
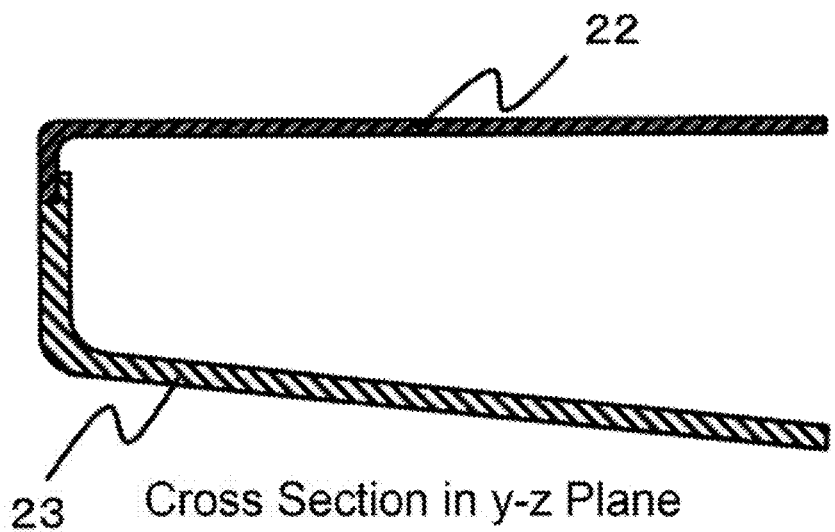
FIG. 13*c* is a sectional view showing an example of a sectional shape taken on y-z plane in FIG. 13*a*.

Next, ABS resin ("TOYOLAC®" 600-309 made by TORAY Industries, Inc.) was molded into a resin sheet having a thickness of 3 mm by extrusion molding, and the resin sheet was vacuum-molded to obtain a molded product having standing wall surfaces on three sides in the outer circumference thereof. The standing wall surfaces of the molded product were processed by a numerical control (NC) router to obtain a resin member 23a (second member 23) which formed the surface C 12 and parts of the surfaces B 11 provided erectly on three sides in the outer circumference of the surface C 12, and had a step portion on the surface B 11 side (FIG. 12a and FIG. 12b). The carbon fiber composite material member 22a and the resin member 23a obtained thus were bonded in the aforementioned step portion by use of a two-liquid epoxy adhesive agent as shown in FIG. 13a, FIG. 13b and FIG. 13c. Thus, a mammography apparatus imaging table 1C was obtained.

The obtained mammography apparatus imaging table 1C had an opening portion 8 in one surface. Further, coupling members 14 made of an aluminum alloy were bonded in the same manner as in (Example 1). The mammography apparatus imaging table 1C was assembled to a mammography apparatus body 2, and a mammography image was taken. The obtained image was good in quality.

According to the method described in the aforementioned [Measurement of Aluminum Equivalent], the aluminum equivalent of the surface A (X-ray irradiation surface 5) was measured. As a result, the aluminum equivalent was 0.17 mmAL on the condition of the X-ray irradiation tube voltage of 60 kV, and 0.14 mmAL on the condition of 20 kV. In addition, in the mammography apparatus imaging table 1C, the specific bending elastic modulus obtained in the same manner as in (Example 1) was 2.71. In addition, the thickness of the surface A (X-ray irradiation surface 5) in the obtained mammography apparatus imaging table 1C was 1.28 mm.

Example 4

The unidirectional carbon fiber prepreg 13 was laminated with a lamination configuration [0/90/0/90/0/0/90/0/90/0], and one layer of a carbon fiber woven fabric prepreg was deposited on one surface of the unidirectional carbon fiber prepreg 13 to obtain a laminate 15. A carbon fiber composite material member 22b (first member 22) was obtained in the same manner as in (Example 3), except that heat and pressure was applied in the double-surface molds in a state where the carbon fiber woven fabric prepreg surface was brought into contact with the female mold surface. Next, polycarbonate resin ("Lupilon®" E-2000, made by Mitsubishi Engineering-Plastics Corporation) was molded into a resin sheet having a thickness of 3 mm by extrusion molding, and the resin sheet was vacuum-molded to obtain a molded product having three standing wall surfaces.

The standing wall surfaces of the molded product were processed by a numerical control (NC) router to obtain a resin member 23b (second member 23) which formed the surface C 12 and parts of the surfaces B 11 provided erectly on three sides in the outer circumference of the surface C 12, and had a step portion on the surface B 11 side. The carbon fiber composite material member 22b and the resin member 23b were bonded in the aforementioned step portion by use of a two-liquid epoxy adhesive agent as shown in FIG. 13a, FIG. 13b and FIG. 13c.

Thus, a mammography apparatus imaging table 1D was obtained. The mammography apparatus imaging table 1D had an opening portion 8. Further, coupling members 14 made of an aluminum alloy were bonded in the same manner as in (Example 1) (FIG. 13a, FIG. 13b and FIG. 13c). The mammography apparatus imaging table 1D was assembled to a mammography apparatus body 2, and a mammography image was taken. The obtained image was good in quality.

According to the method described in the aforementioned [Measurement of Aluminum Equivalent], the aluminum equivalent of the surface A (X-ray irradiation surface 5) was measured. As a result, the aluminum equivalent was 0.18 mmAL on the condition of the X-ray irradiation tube voltage of 60 kV, and 0.15 mmAL on the condition of 20 kV. In addition, in the mammography apparatus imaging table 1D, the specific bending elastic modulus obtained in the same manner as in (Example 1) was 2.75. In addition, the thickness of the surface A (X-ray irradiation surface 5) in the obtained mammography apparatus imaging table 1D was 1.30 mm.

Example 5

The unidirectional carbon fiber prepreg 13 was cut to have a width of 10 mm so that the longitudinal direction thereof coincided with the orientation direction of fibers. Thus, a unidirectional carbon fiber tape was obtained. The unidirectional carbon fiber tape was set in an automatic lamination apparatus. By use of the same single-surface mold 9 as in (Example 1), the unidirectional carbon fiber tape was shaped with a configuration $[0/90]_{3S}$ from the mold surface side by the automatic lamination apparatus. In the shaping step, the unidirectional carbon fiber tape was shaped without forming a seam among standing wall surfaces and with uniform thickness in any corner portion. In the same method as in (Example 1) except for the above, a mammography apparatus imaging stand 1E was obtained. The mammography apparatus imaging table 1E had an opening portion 8. Coupling members 14 made of an aluminum alloy were bonded in the same manner as in (Example 1) (FIG. 8a, FIG. 8b and FIG. 8c). The mammography apparatus imaging table 1E was assembled to a mammography apparatus body 2, and a mammography image was taken. The obtained image was good in quality.

According to the method described in the aforementioned [Measurement of Aluminum Equivalent], the aluminum equivalent of the surface A (X-ray irradiation surface 5) was measured. As a result, the aluminum equivalent was 0.17 mmAL on the condition of the X-ray irradiation tube voltage of 60 kV, and 0.14 mmAL on the condition of 20 kV. In addition, in the mammography apparatus imaging table 1E, the specific bending elastic modulus obtained in the same manner as in (Example 1) was 2.68. In addition, the thickness of the surface A (X-ray irradiation surface 5) in the obtained mammography apparatus imaging table 1E was 1.28 mm.

Comparative Example 1

A mammography apparatus imaging table 1F was obtained in the same method as in (Example 1), except that 7 layers of the carbon fiber woven fabric prepreg were used to be shaped on the mold. The mammography apparatus imaging table 1F had an opening portion 8. Coupling members 14 made of an aluminum alloy were bonded in the same manner as in (Example 1) (FIG. 8a, FIG. 8b and FIG. 8c). The mammography apparatus imaging table 1F was assembled to a mammography apparatus body 2, and a mammography image was taken. The image was obtained without any problem. According to the method described in the aforementioned [Measurement of Aluminum Equivalent], the aluminum equivalent of the surface A (X-ray irradiation surface 5) was measured. As a result, the aluminum equivalent was 0.20 mmAL on the condition of the X-ray irradiation tube voltage of 60 kV, and 0.16 mmAL on the condition of 20 kV. In addition, in the mammography apparatus imaging table 1F, the specific bending elastic modulus obtained in the same manner as in (Example 1) was 2.46. In addition, the thickness of the surface A (X-ray irradiation surface 5) in the obtained mammography apparatus imaging table 1F was 1.45 mm.

The characteristics of the imaging tables for the mammography apparatus obtained in the aforementioned Examples and Comparative Examples are listed in Table 1. As compared with the mammography apparatus imaging table 1F, it was confirmed that the mammography apparatus imaging table 1A was a mammography apparatus imaging table in which the thickness of the X-ray irradiation surface was reduced, and the rigidity and the X-ray transparency were high. In addition, the surface of each of the mammography apparatus imaging table 1A and the mammography apparatus imaging table 1B was polished with sand paper to expose the carbon fibers. When the surface was traced with a bare hand, fluff of the carbon fibers hitched fingers to give a feeling of pain in the mammography apparatus imaging table 1A. However, there was no feeling of pain in the mammography apparatus imaging table 1B. In the mammography apparatus imaging table 1C, the number of cutting patterns for cutting a base material was reduced while the rigidity and the X-ray transparency were kept as high as those in the mammography apparatus imaging table 1A. Thus, the mammography apparatus imaging table 1C was manufactured with good productivity. The mammography apparatus imaging table 1E was manufactured with good productivity due to the automation of the lamination step on the single-surface mold, as compared with the mammography apparatus imaging table 1A.

Example 11

As a resin sheet, a resin sheet having a thickness of 1.2 mm was obtained by acid-modified polypropylene resin ("Admer®" QB510, made by Mitsui Chemicals, Inc.), by an extruder. The resin sheet 25 and a carbon fiber woven fabric prepreg 24 were deposited on the single-surface mold 9 shown in FIG. 4. The single-surface mold 9 had a surface A 10 for forming a top surface including an X-ray irradiation surface, three surfaces (B 11) for forming standing wall surfaces of side surfaces of a mammography apparatus imaging table 1A, and a surface C 12 for forming a bottom surface of the mammography apparatus imaging table 1A. A step of imparting the shape of the single-surface mold 9 to the carbon fiber woven fabric prepreg 24 and the resin sheet 25 was carried out by a method in which the layers thereof were deposited on the single-surface mold 9 one by one.

Figure 14:
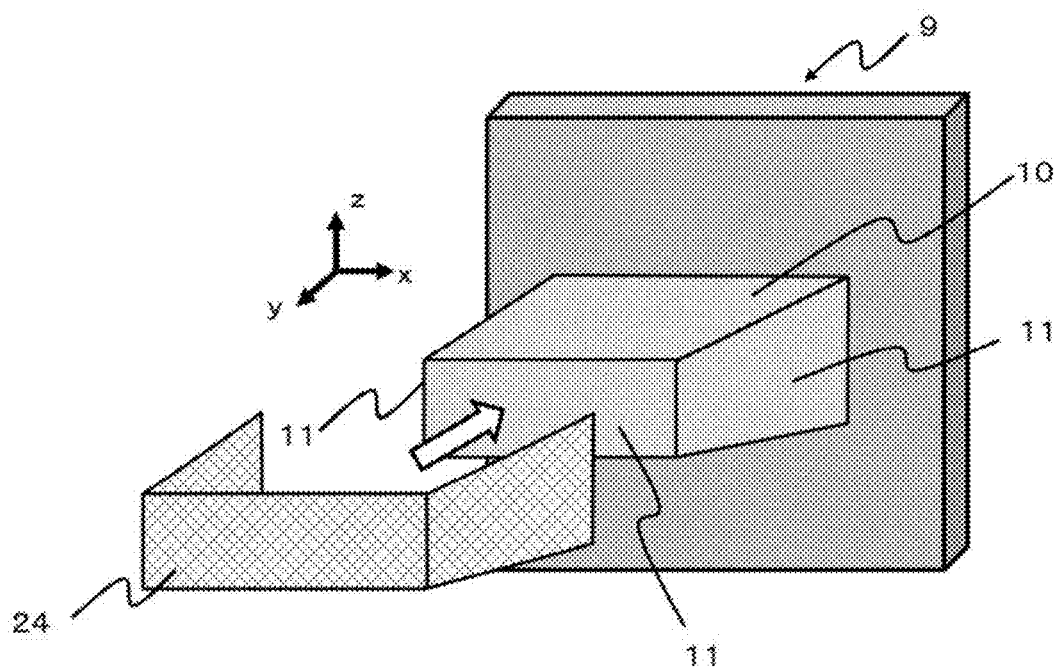
FIG. 14 is a schematic view showing an example of a step of the method for manufacturing the imaging table for the mammography apparatus according to the embodiment of the present invention.
Figure 15:
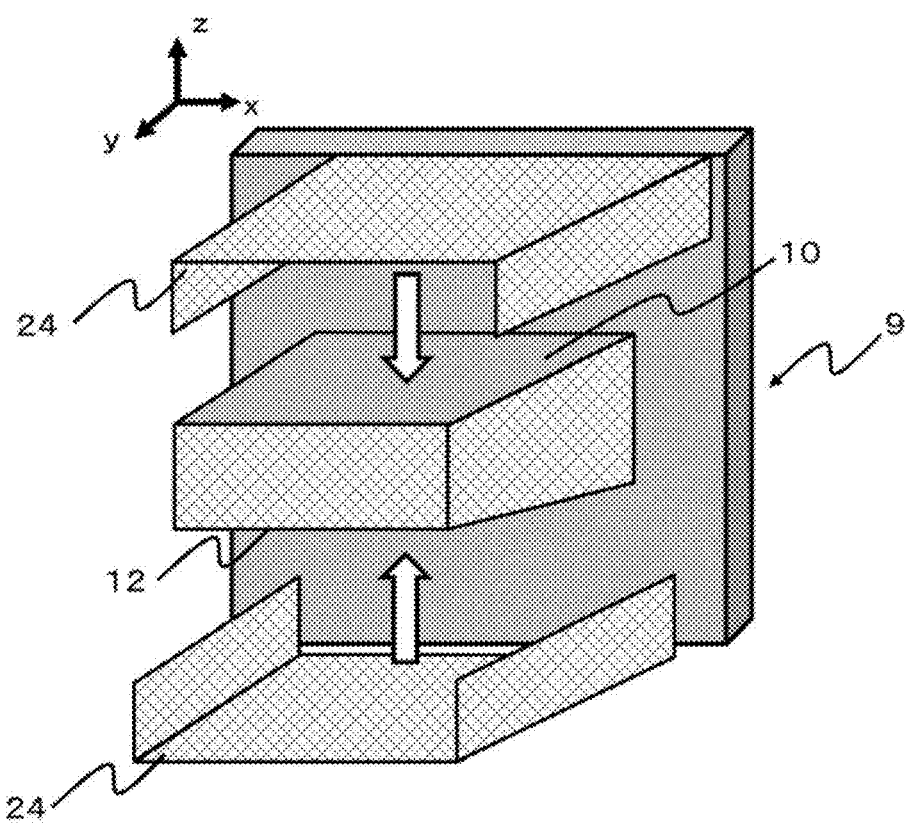
FIG. 15 is a schematic view showing an example of a step of the method for manufacturing the imaging table for the mammography apparatus according to the embodiment of the present invention.
Figure 16:
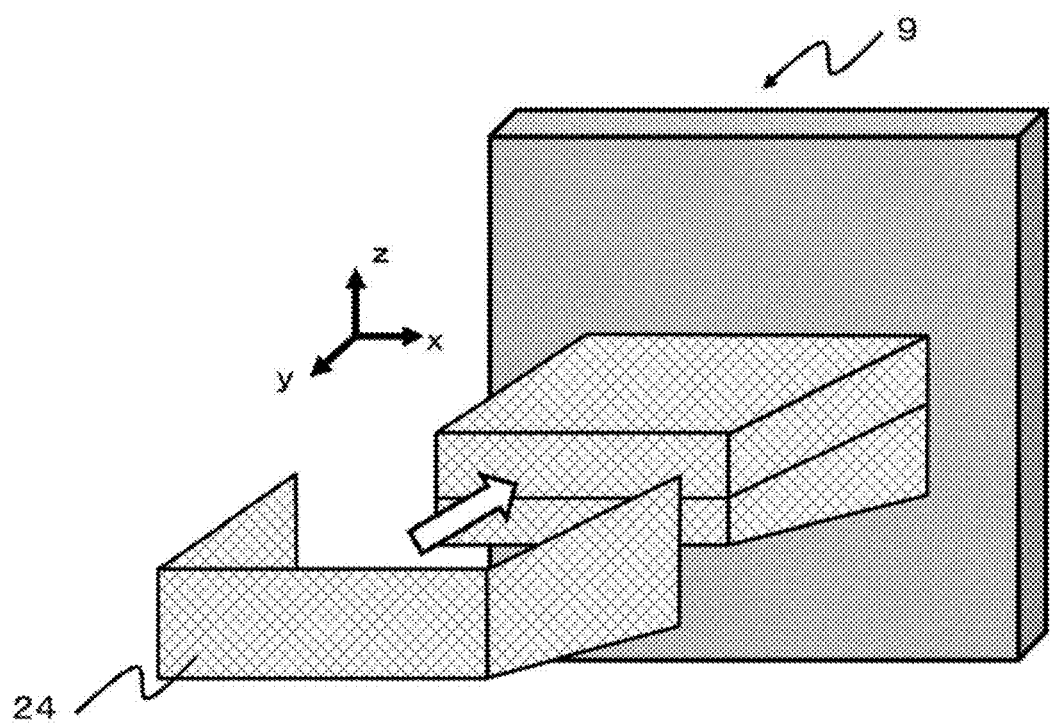
FIG. 16 is a schematic view showing an example of a step of the method for manufacturing the imaging table for the mammography apparatus according to the embodiment of the present invention.

First, the carbon fiber woven fabric prepreg 24 was deposited on the surfaces B 11 (FIG. 14). After that, the carbon fiber woven fabric prepreg 24 was deposited on the surface A 10 with a lamination configuration [2 layers of carbon fiber woven fabric prepreg/resin sheet/2 layers of carbon fiber woven fabric prepreg], and 7 layers of the carbon fiber woven prepreg 24 were deposited on the surface C 12 (FIG. 15). Finally, the carbon fiber woven fabric prepreg 24 was deposited on the surfaces B 11 (FIG. 16). In the aforementioned lamination configuration, the resin sheet 25 had the same dimensions as the surface A. The carbon fiber woven fabric prepreg 24 in this lamination configuration was cut by three kinds of cutting patterns, that is, a cutting pattern for deposition on the surface A 10, a cutting pattern for deposition on the surfaces B 11, and a cutting pattern for deposition on the surface C 12. The outer circumference of the region where the carbon fiber woven fabric prepreg 24 had been deposited was covered with a seal material 18 (bringing a flexible film 16 into close contact with the mold to thereby tightly close the mold). After that, a bleeder 17 (playing a role of a spacer serving as an air passage) made of a thick nonwoven fabric was disposed on an outer circumferential portion of the prepreg laminate 15 as shown in FIG. 9.

A valve 19 provided with a check valve was disposed as a suction opening on the bleeder 17. After that, the single-surface mold was covered with the flexible film 16, and the seal material 18 and the flexible film 16 were brought into close contact with each other. After that, a vacuum pump was connected to the valve 19 serving as a suction opening so as to suck the air from a molding space (a space formed by the single-surface mold and the flexible film 16 and including the region where the carbon fiber woven fabric prepreg 24 and the resin sheet 25 had been deposited), thereby reducing the pressure in the molding space. After that, the single-surface mold was thrown into an autoclave apparatus. The temperature of the single-surface mold was increased at a rate of 2.5° C./min under the condition of 3 atm. After the temperature reached 130° C., the single-surface mold was retained for 90 minutes. By heating and pressurizing the single-surface mold in this manner, the thermosetting resin composition in the carbon fiber woven fabric prepreg 24 was cured. After molding, a molded product was released from the single-surface mold 9. End faces of the molded product were trimmed by a numerical control (NC) router to obtain a mammography apparatus imaging table 1G.

The obtained mammography apparatus imaging table 1G had an opening portion.

Figure 17A:
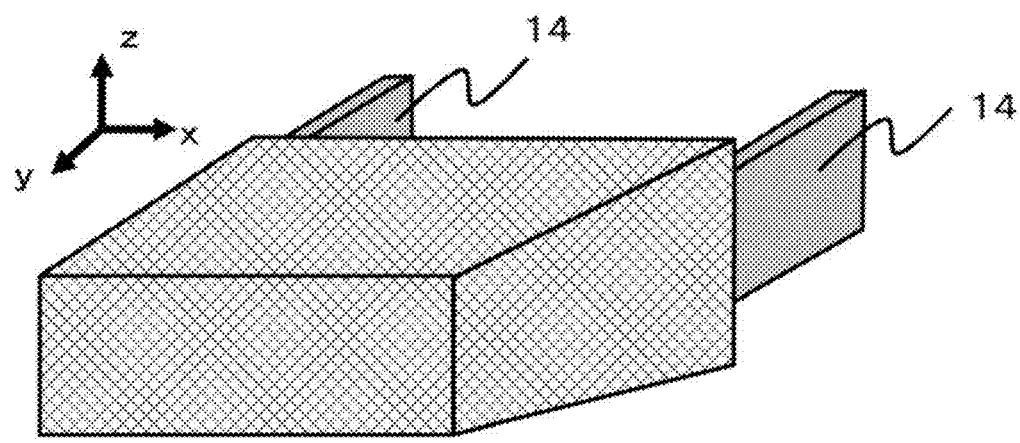
FIG. 17*a* is a schematic view showing an example of the external appearance and a sectional shape of the imaging table for the mammography apparatus according to the embodiment of the present invention.
Figure 17B:
FIG. 17*b* is a sectional view showing an example of a sectional shape taken on x-z plane in FIG. 17*a*.
Figure 17C:
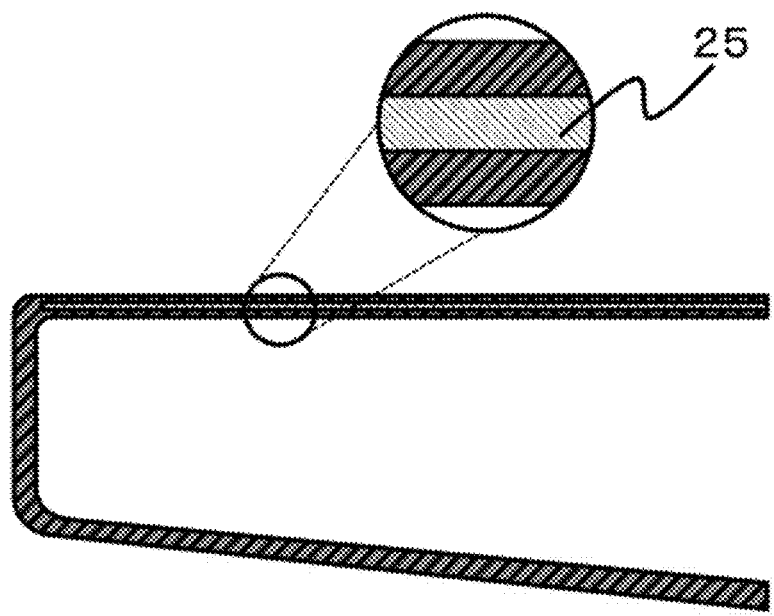
FIG. 17*c* is a sectional view showing an example of a sectional shape taken on y-z plane in FIG. 17*a*.

Coupling members 14 made of an aluminum alloy were inserted through the opening portion, and bonded to inner wall surfaces of two standing wall portions opposed to each other so as to form the opening portion, respectively, by use of a two-liquid epoxy adhesive agent (FIG. 17a, FIG. 17b and FIG. 17c). The mammography apparatus imaging table 1G was assembled to a mammography apparatus body 2, and a mammography image was taken. The obtained image was good in quality. The aluminum equivalent of the X-ray irradiation surface was measured. As a result, the aluminum equivalent was 0.19 mmAL on the condition of the X-ray irradiation tube voltage of 60 kV, and 0.15 mmAL on the condition of 20 kV. In addition, a rectangular test piece was cut out from the X-ray irradiation surface of the obtained mammography apparatus imaging table 1G by use of a numerical control (NC) router so that the x-direction thereof was set as the longitudinal direction. The specific bending elastic modulus calculated by the method described in [Calculation of Specific Bending Elastic Modulus Ep] was 2.93.

Example 12

As a resin sheet, a resin sheet having a thickness of 1.2 mm was obtained by acid-modified polypropylene resin ("Admer®" QB510, made by Mitsui Chemicals, Inc.), by an extruder. Two sets of pieces in each of which two layers of a carbon fiber woven fabric prepreg had been deposited were prepared and deposited on the opposite sides of the resin sheet respectively to obtain a laminate. The laminate was disposed in a pair of double-surface molds, that is, a female mold 20 and a male mold 21 shown in FIG. 10. The laminate was heated and pressurized at a surface pressure of 1.0 MPa at 130° C. for 90 minutes by use of a hydraulic pressing machine to obtain a molded product. The surface pressure was calculated from an area (projected area viewed from the lamination direction) of the laminate before molding.

Figure 18A:
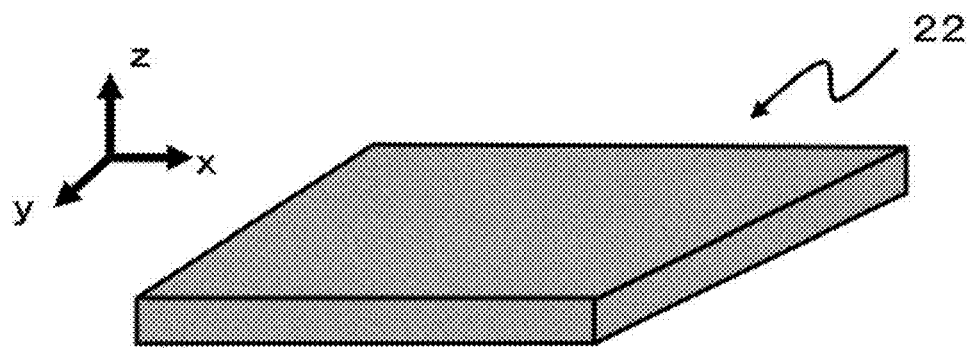
FIG. 18*a* is a schematic view showing an example of the external appearance of the first member constituting the imaging table for the mammography apparatus according to the embodiment of the present invention.
Figure 18B:
FIG. 18*b* is a sectional view showing an example of a sectional shape taken on y-z plane in FIG. 18*a*.

The outer circumference of the molded product was trimmed by a numerical control (NC) router to obtain a first member 22H including a skin material including the carbon fiber composite material and a core material including the resin sheet (FIG. 18a and FIG. 18b). Polycarbonate resin pellet ("Panlite®" G-3420 made by Teijin Limited) was used as a raw material to mold a second member 23H having a shape in FIG. 12a and FIG. 12b by use of an injection molding machine. The first member 22H and the second member 23H obtained thus were bonded by use of a two-liquid epoxy adhesive agent. Thus, a mammography apparatus imaging table 1H was obtained.

Figure 19A:
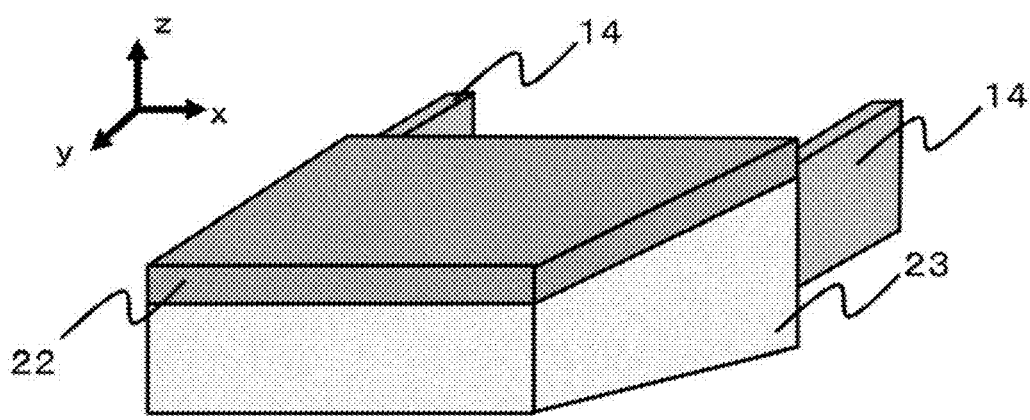
FIG. 19*a* is a schematic view showing an example of the external appearance of the imaging table for the mammography apparatus according to the embodiment of the present invention.
Figure 19B:
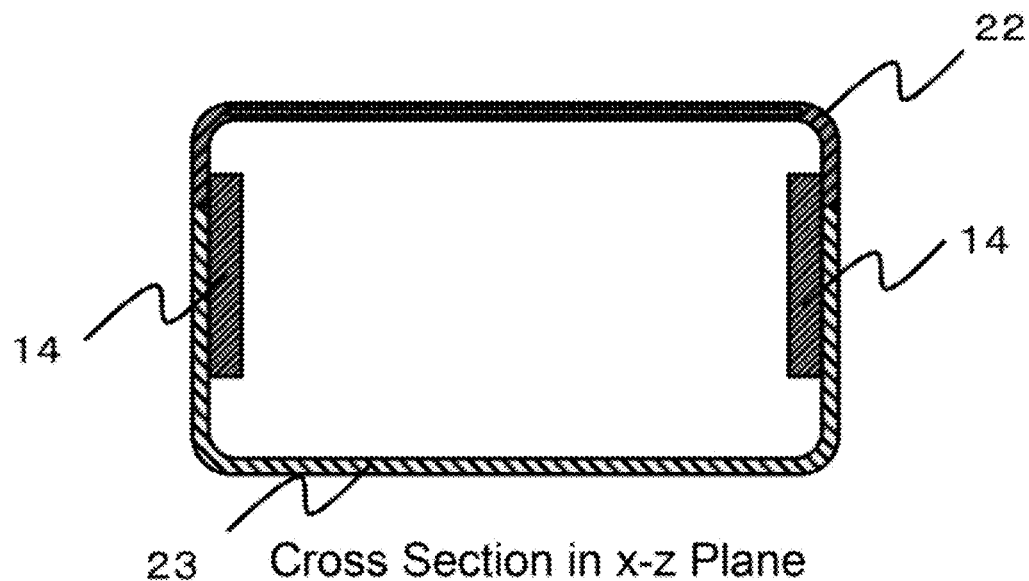
FIG. 19*b* is a sectional view showing an example of a sectional shape taken on x-z plane in FIG. 19*a*.
Figure 19C:
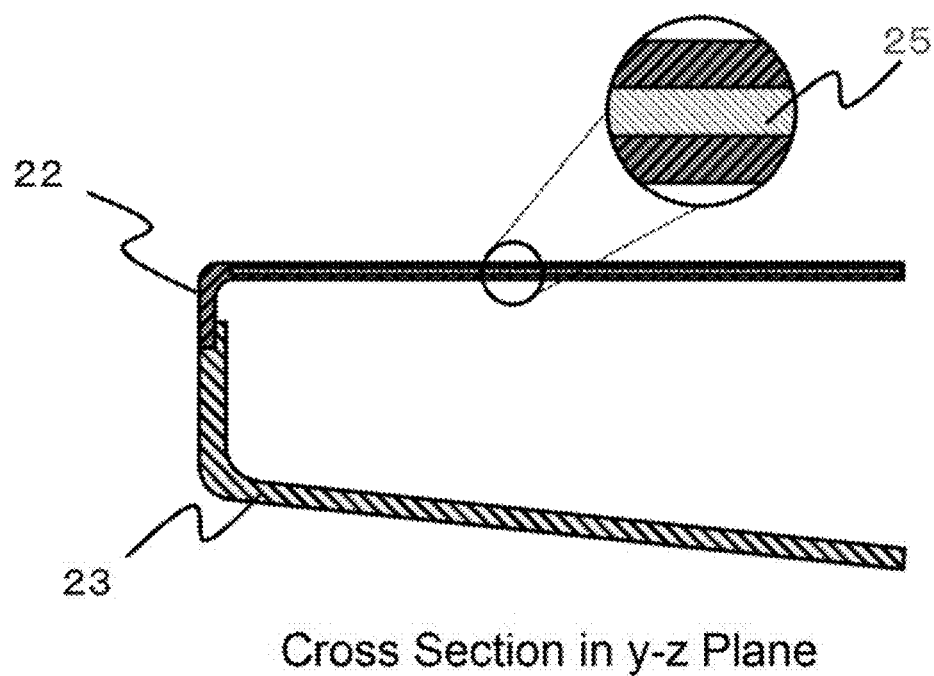
FIG. 19*c* is a sectional view showing an example of a sectional shape taken on y-z plane in FIG. 19*a*.

The obtained mammography apparatus imaging table 1H had an opening portion. Further, coupling members 14 made of an aluminum alloy were bonded in the same manner as in (Example 11) (FIG. 19a, FIG. 19b and FIG. 19c). The mammography apparatus imaging table 1H was assembled to a mammography apparatus body 2, and a mammography image was taken. The obtained image was good in quality. According to the method described in the aforementioned [Measurement of Aluminum Equivalent], the aluminum equivalent of the X-ray irradiation surface was measured. As a result, the aluminum equivalent was 0.19 mmAL on the condition of the X-ray irradiation tube voltage of 60 kV, and 0.15 mmAL on the condition of 20 kV. In addition, a rectangular test piece was cut out from the X-ray irradiation surface of the first member 22H in the obtained mammography apparatus imaging table 1H by use of a numerical control (NC) router so that the x-direction thereof was set as the longitudinal direction. The specific bending elastic modulus calculated by the method described in [Calculation of Specific Bending Elastic Modulus Ep] was 2.93.

Example 13

As a resin sheet, acrylic foam ("Foamac®" S #1000, made by Sekisui Chemical Co., Ltd.) was cut out to obtain a resin sheet having a thickness of 1.5 mm. The resin sheet and the unidirectional carbon fiber prepreg were deposited with a lamination configuration [0/90/resin sheet/90/0] to obtain a laminate. The x-direction shown in FIG. 19a corresponded to the direction of 0° in the aforementioned lamination configuration. A mammography apparatus imaging table 1I including a first member 22I and a second member 23I was obtained in the same manner as in (Example 12), except that the laminate obtained thus was used. The obtained mammography apparatus imaging table 1I had an opening portion. Further, coupling members 14 made of an aluminum alloy were bonded in the same manner as in (Example 12) (FIG. 19a, FIG. 19b and FIG. 19c). The mammography apparatus imaging table 1I was assembled to a mammography apparatus body 2, and a mammography image was taken. The obtained image was good in quality.

According to the method described in the aforementioned [Measurement of Aluminum Equivalent], the aluminum equivalent of the X-ray irradiation surface was measured. As a result, the aluminum equivalent was 0.12 mmAL on the condition of the X-ray irradiation tube voltage of 60 kV, and 0.11 mmAL on the condition of 20 kV. In addition, a rectangular test piece was cut out from the X-ray irradiation surface of the first member 22I in the obtained mammography apparatus imaging table 1I by use of a numerical control (NC) router so that the x-direction thereof was set as the longitudinal direction. The specific bending elastic modulus calculated by the method described in [Calculation of Specific Bending Elastic Modulus Ep] was 7.13. The ratio between the major diameter and the minor diameter of closed cells evaluated according to the method described in the aforementioned [Measurement of Ratio (minor diameter/major diameter) between Major Diameter and Minor Diameter of Closed Cell] and [Measurement of Angle between minor axis and thickness-direction axis] was 0.58, the average minor diameter was 123 μm, and the angle between the minor axis and the thickness-direction axis was 53°.

Example 14

As a resin sheet, polymethacrylimide foam ("Rohacell®" 110HP made by Daicel-Evonik Ltd.) was cut out to obtain a resin sheet having a thickness of 1.5 mm. The resin sheet and the unidirectional carbon fiber prepreg were deposited with a lamination configuration [0/90/resin sheet/90/0] to obtain a laminate. In the lamination configuration, the direction of 0° corresponded to the fiber orientation direction of the unidirectional carbon fibers, and the x-direction shown in FIG. 19 corresponded to the direction of 0°. A first member 22J was obtained in the same manner as in (Example 12), except that the aforementioned laminate was used.

Next, by ABS resin ("TOYOLAC®" 600-309 made by TORAY Industries, Inc.), a resin sheet having a thickness of 3 mm was produced by extrusion molding, and the resin sheet was vacuum-molded to obtain a molded product having standing wall surfaces.

The standing wall surfaces of the molded product were processed by a numerical control (NC) router to obtain a second member 23J which had a step portion in an end portion of each of the standing walls. The first member 22J and the second member 23J obtained thus were bonded by use of a two-liquid epoxy adhesive agent to obtain a mammography apparatus imaging table 1J. The obtained mammography apparatus imaging table 1J had an opening portion. Further, coupling members 14 made of an aluminum alloy were bonded in the same manner as in (Example 12) (FIG. 19a, FIG. 19b and FIG. 19c). The mammography apparatus imaging table 1J was assembled to a mammography apparatus body 2, and a mammography image was taken. The obtained image was good in quality. According to the method described in the aforementioned [Measurement of Aluminum Equivalent], the aluminum equivalent of the X-ray irradiation surface was measured. As a result, the aluminum equivalent was 0.12 mmAL on the condition of the X-ray irradiation tube voltage of 60 kV, and 0.10 mmAL on the condition of 20 kV.

In addition, a rectangular test piece was cut out from the X-ray irradiation surface of the first member 22J in the obtained mammography apparatus imaging table 1J by use of a numerical control (NC) router so that the x-direction thereof was set as the longitudinal direction. The specific bending elastic modulus calculated by the method described in [Calculation of Specific Bending Elastic Modulus Ep] was 7.54. The ratio between the major diameter and the minor diameter of closed cells evaluated according to the method described in the aforementioned [Measurement of Ratio (minor diameter/major diameter) between Major Diameter and Minor Diameter of Closed Cell] and [Measurement of Angle between minor axis and thickness-direction axis] was 0.75, the average minor diameter was 209 μm, and the angle between the minor axis and the thickness-direction axis was 24°.

Example 15

The unidirectional carbon fiber prepreg and the resin sheet used in (Example 14) were deposited with a lamination configuration [0/90/resin sheet/90/0], and a layer of the carbon fiber woven fabric prepreg was deposited on one side of the resin sheet to obtain a laminate. In the aforementioned lamination configuration, the x-direction shown in FIG. 19a corresponded to the direction of 0°. The laminate was disposed in a pair of double-surface molds, that is, a female mold 20 and a male mold 21 shown in FIG. 10 so as to bring the carbon fiber woven fabric prepreg surface into contact with the female mold surface. The laminate was heated and pressurized at a surface pressure of 1.0 MPa at 130° C. for 90 minutes by use of a hydraulic pressing machine to obtain a molded product.

The outer circumference of the molded product was trimmed by a numerical control (NC) router to obtain a first member 22K including a skin material including the carbon fiber composite material and a core material including the resin sheet. The surface pressure was calculated from an area (projected area viewed from the lamination direction) of the laminate which had not been molded yet. A mammography apparatus imaging table 1K including the first member 22K and the second member 23K was obtained in the same method as in (Example 14) except for the above.

The obtained mammography apparatus imaging table 1K had an opening portion. Further, coupling members 14 made of an aluminum alloy were bonded in the same manner as in (Example 12) (FIG. 19a, FIG. 19b and FIG. 19c). The mammography apparatus imaging table 1K was assembled to a mammography apparatus body 2, and a mammography image was taken. The obtained image was good in quality. According to the method described in the aforementioned [Measurement of Aluminum Equivalent], the aluminum equivalent of the X-ray irradiation surface was measured. As a result, the aluminum equivalent was 0.13 mmAL on the condition of the X-ray irradiation tube voltage of 60 kV, and 0.12 mmAL on the condition of 20 kV. In addition, a rectangular test piece was cut out from the X-ray irradiation surface of the first member 22K in the obtained mammography apparatus imaging table 1K by use of a numerical control (NC) router so that the x-direction thereof was set as the longitudinal direction. The specific bending elastic modulus calculated by the method described in [Calculation of Specific Bending Elastic Modulus Ep] was 6.32. The ratio between the major diameter and the minor diameter of closed cells evaluated according to the method described in the aforementioned [Measurement of Ratio (minor diameter/major diameter) between Major Diameter and Minor Diameter of Closed Cell] and [Measurement of Angle between minor axis and thickness-direction axis] was 0.62, the average minor diameter was 178 μm, and the angle between the minor axis and the thickness-direction axis was 18°.

Comparative Example 11

By use of the same single-surface mold 9 as in (Example 11), the shape of the mold was imparted to 7 layers of the carbon fiber woven fabric prepreg from the mold surface thereof. A mammography apparatus imaging table 1L was obtained in the same method as in (Example 11) except for the above. The obtained mammography apparatus imaging table 1L had an opening portion. Further, coupling members 14 made of an aluminum alloy were bonded in the same manner as in (Example 11) (FIG. 17a, FIG. 17b and FIG. 17c). The mammography apparatus imaging table 1L was assembled to a mammography apparatus body 2, and a mammography image was taken. The obtained image was good in quality. According to the method described in the aforementioned [Measurement of Aluminum Equivalent], the aluminum equivalent of the surface A (X-ray irradiation surface 5) was measured. As a result, the aluminum equivalent was 0.20 mmAL on the condition of the X-ray irradiation tube voltage of 60 kV, and 0.16 mmAL on the condition of 20 kV. In addition, a rectangular test piece was cut out by use of a numerical control (NC) router so that the x-direction of the obtained mammography apparatus imaging table 1L was set as the longitudinal direction. The specific bending elastic modulus calculated by the method described in [Calculation of Specific Bending Elastic Modulus Ep] was 2.46.

Example 16

Spinning, baking and surface oxidization were performed on a copolymer containing polyacrylonitrile as a main component to obtain continuous carbon fibers having the total number of single filament of 12,000. As for the properties of the continuous carbon fibers, a single-fiber diameter was 7 µm, density was 1.8 g/cm$^3$, tensile strength was 4,600 MPa, and tensile elasticity was 220 GPa. The obtained continuous carbon fibers were cut to have a length of 6 mm by a cartridge cutter to obtain chopped carbon fibers. A dispersion liquid consisting of water and surfactant (Polyoxyethylene Lauryl Ether (tradename), made by Nacalai Tesque, Inc.) and having a concentration of 0.1% by mass was produced. Papermaking was performed on the dispersion liquid and the chopped carbon fibers. A papermaking apparatus includes a cylindrical vessel having a diameter of 1,000 mm and serving as a dispersion tank, and a straight-line transport portion (with an inclination angle of 30°). The vessel had an opening cock in a lower portion of the vessel. The transport portion connected the dispersion tank to a papermaking tank. A stirrer pertained to an opening portion in an upper portion of the dispersion tank. Through the opening portion, the chopped carbon fibers and the dispersion liquid (dispersion medium) could be thrown. The papermaking tank was provided with a mesh conveyor having a papermaking surface having a width of 500 mm in a bottom portion thereof. The mesh conveyor was configured to convey a carbon fiber base material (papermaking base material) obtained therefrom. Papermaking was performed with a carbon fiber concentration of 0.05% by mass in the dispersion liquid. The carbon fiber base material subjected to the papermaking was dried in a drying furnace at 200° C. for 30 minutes to obtain a reinforced fiber mat. The obtained basis weight was 25 g/m$^2$.

A resin film having a basis weight of 50 g/m$^2$, which was composed of 80% by mass of unmodified polypropylene resin ("Prime Polypro" J105G, made by Prime Polymer Co., Ltd.) and 20% by mass of acid-modified polypropylene resin ("Admer®" QB510, made by Mitsui Chemicals, Inc.), was produced.

A laminate in which reinforced fiber mats and resin sheets were disposed in order of [resin film/reinforced fiber mat/resin film/reinforced fiber mat/reinforced fiber mat/resin film/reinforced fiber mat/resin film] was produced. Next, a resin sheet having a thickness of 1.5 mm and a density of 0.2 g/cm$^3$ was obtained through the following steps (I) to (V).

From observation of a section of the obtained resin sheet, it was confirmed that reinforced fibers were dispersed like substantial monofilaments and at random, and voids were provided due to the reinforced fibers serving as columnar supports.

(I) The laminate was disposed in a cavity of a mold for press molding preheated to 230° C., and the mold was closed.
(II) Next, the laminate was retained for 120 seconds, and further retained for 60 seconds with a pressure of 3 MPa applied thereto.
(III) After the step (II), the mold cavity was opened, and a metal spacer was inserted to a terminal thereof so that the thickness of a structure to be obtained was adjusted to 1.5 mm.
(IV) After that, the mold cavity was fastened again, and the cavity temperature was cooled down to 50° C. in a state where the pressure was maintained.
(V) The mold was opened and the resin sheet was extracted.

The resin sheet and the unidirectional carbon fiber prepreg were deposited with a lamination configuration [0/90/resin sheet/90/0] to obtain a laminate. The x-direction shown in FIG. 19a corresponded to the direction of 0° in the aforementioned lamination configuration. The resin sheet and the unidirectional carbon fiber prepreg were disposed in the pair of double-surface molds, that is, a female mold 20 and a male mold 21 shown in FIG. 10. The laminate was heated and pressurized at a surface pressure of 3.0 MPa at 160° C. for 30 minutes by use of the hydraulic pressing machine to obtain a molded product.

The outer circumference of the molded product was trimmed by a numerical control (NC) router to obtain a first member 22M including a skin material including the carbon fiber composite material and a core material including the resin sheet. The surface pressure was calculated from an area (projected area viewed from the lamination direction) of the laminate before molding. In the same method as in (Example 14) except for the above, a mammography apparatus imaging table 1M including the first member 22M and a second member 23M was obtained.

The obtained mammography apparatus imaging table 1M had an opening portion. Further, coupling members 14 made of an aluminum alloy were bonded in the same manner as in (Example 12) (FIG. 19a, FIG. 19b and FIG. 19c). The mammography apparatus imaging table 1M was assembled to a mammography apparatus body 2, and a mammography image was taken. The obtained image was good in quality. According to the method described in the aforementioned [Measurement of Aluminum Equivalent], the aluminum equivalent of the X-ray irradiation surface was measured. As a result, the aluminum equivalent was 0.12 mmAL on the condition of the X-ray irradiation tube voltage of 60 kV, and 0.10 mmAL on the condition of 20 kV. In addition, a rectangular test piece was cut out from the X-ray irradiation surface of the first member 22M in the obtained mammography apparatus imaging table 1M by use of a numerical control (NC) router so that the x-direction thereof was set as the longitudinal direction. The specific bending elastic modulus calculated by the method described in [Calculation of Specific Bending Elastic Modulus Ep] was 7.70.

Example 17

A laminate in which the reinforced fiber mats and the resin sheets produced in (Example 16) were disposed in order of [resin film/reinforced fiber mat/resin film/reinforced fiber mat/resin film/reinforced fiber mat/resin film/reinforced fiber mat/reinforced fiber mat/resin film/reinforced fiber mat/resin film/reinforced fiber mat/resin film/reinforced fiber mat/resin film] was produced. Next, a resin sheet having a thickness of 3.0 mm and a density of 0.2 g/cm$^3$ was obtained through the following steps (I) to (V). From observation of a section of the obtained resin sheet, it was confirmed that the reinforced fibers were dispersed like substantial monofilaments and at random, and the obtained resin sheet included voids where reinforced fibers served as columnar supports.

(I) The laminate was disposed in a cavity of a press-molding mold preheated to 230° C., and the mold was closed.
(II) Next, the laminate was retained for 120 seconds, and further retained for 60 seconds with a pressure of 3 MPa applied thereto.
(III) After the step (II), the mold cavity was opened, and a metal spacer was inserted to a terminal thereof so that the thickness of a structure to be obtained was adjusted to 3.0 mm.
(IV) After that, the mold cavity was fastened again, and the cavity temperature was cooled down to 50° C. in a state where the pressure was maintained.
(V) The mold was opened and the resin sheet was extracted.

Figure 10:
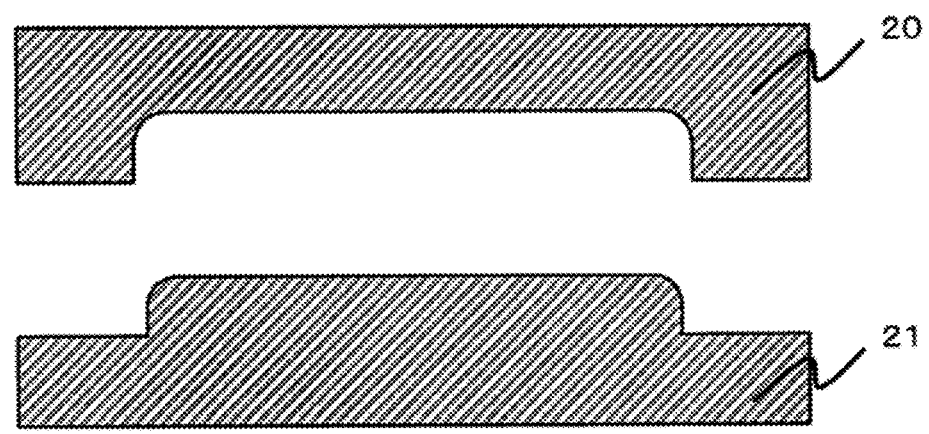
FIG. 10 is a schematic view showing an example of double-surface molds for molding the imaging table for the mammography apparatus according to the embodiment of the present invention.

The resin sheet was disposed in a pair of double-surface molds, that is, a female mold 20 and a male mold 21 shown in FIG. 10. The resin sheet was heated and pressurized at a surface pressure of 3.0 MPa at 180° C. for 5 minutes by use of a hydraulic pressing machine, and then cooled down to 50° C. in a state where the pressure was maintained. Thus, the resin sheet was shaped. After the shaping, a layer of the carbon fiber woven fabric prepreg was deposited on the female mold side of the resin sheet, and disposed in the pair of double-surface molds shown in FIG. 10 again. The laminate was heated and pressurized at a surface pressure of 1.0 MPa at 130° C. for 90 minutes by use of the hydraulic pressing machine to obtain a molded product.

The outer circumference of the molded product was trimmed by a numerical control (NC) router to obtain a first member 22N having a two-layer configuration including a skin material including the carbon fiber composite material, and the resin sheet. The surface pressure was calculated from an area (projected area viewed from the lamination direction) of the laminate which had not been molded yet.

Next, a resin sheet having a thickness of 4.5 mm was produced by ABS resin ("TOYOLAC®" 600-309 made by TORAY Industries, Inc.), by extrusion molding, and the resin sheet was vacuum-molded to obtain a molded product having standing wall surfaces.

Figure 20A:
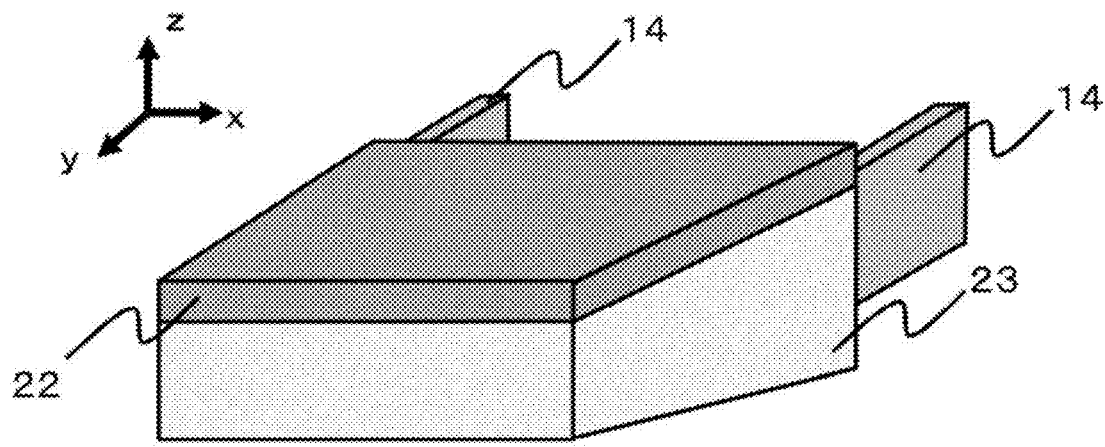
FIG. 20*a* is a schematic view showing an example of the external appearance of the imaging table for the mammography apparatus according to the embodiment of the present invention.
Figure 20B:
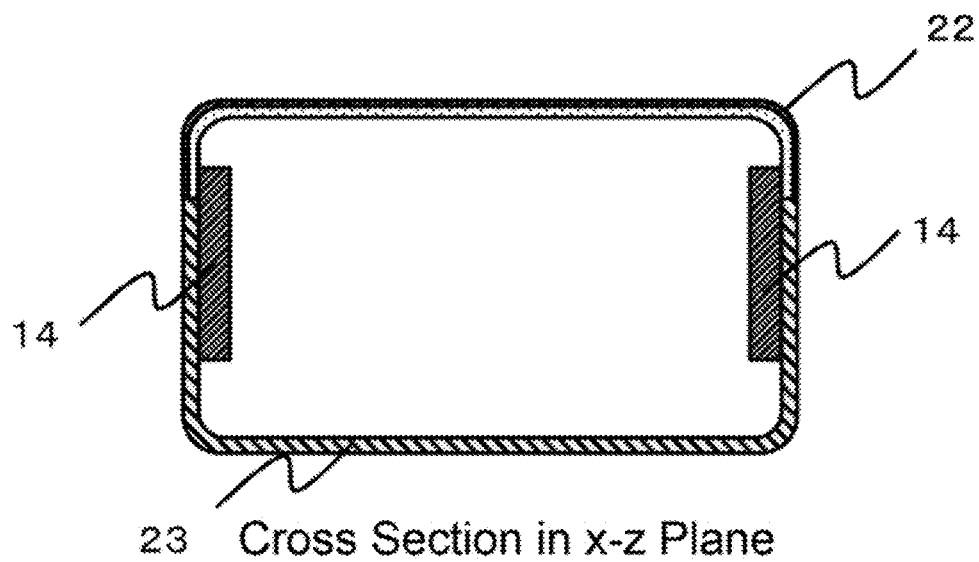
FIG. 20*b* is a sectional view showing an example of a sectional shape taken on x-z plane in FIG. 20*a*.
Figure 20C:
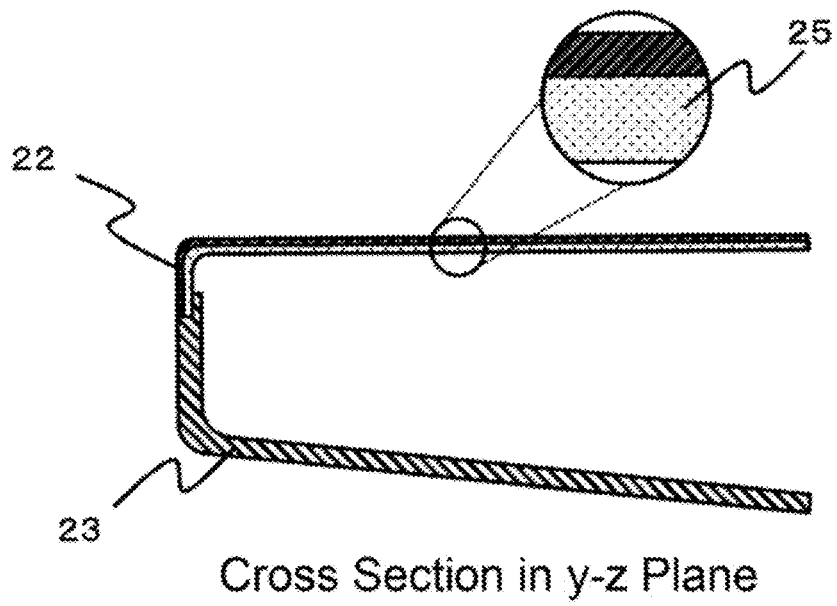
FIG. 20*c* is a sectional view showing an example of a sectional shape taken on y-z plane in FIG. 20*a*.

The standing wall surfaces of the molded product were processed by a numerical control (NC) router to obtain a second member 23N which had a step portion in an end portion of each of the standing walls. The first member 22N and the second member 23N obtained thus were bonded by use of a two-liquid epoxy adhesive agent to obtain a mammography apparatus imaging table 1N. The obtained mammography apparatus imaging table 1N had an opening portion. Further, coupling members 14 made of an aluminum alloy were bonded in the same manner as in (Example 12) (FIG. 20a, FIG. 20b and FIG. 20c). The mammography apparatus imaging table 1N was assembled to a mammography apparatus body 2, and a mammography image was taken. The obtained image was good in quality. According to the method described in the aforementioned [Measurement of Aluminum Equivalent], the aluminum equivalent of the X-ray irradiation surface was measured. As a result, the aluminum equivalent was 0.10 mmAL on the condition of the X-ray irradiation tube voltage of 60 kV, and 0.09 mmAL on the condition of 20 kV. In addition, a rectangular test piece was cut out from the X-ray irradiation surface of the first member 22N of the obtained mammography apparatus imaging table 1N by use of a numerical control (NC) router so that the x-direction thereof was set as the longitudinal direction. The specific bending elastic modulus calculated by the method described in [Calculation of Specific Bending Elastic Modulus Ep] was 11.1.

The characteristics of the imaging tables for the mammography apparatus obtained in the aforementioned Examples and Comparative Examples are listed in Table 2. From comparison between the mammography apparatus imaging table 1G and the mammography apparatus imaging table 1L, it was confirmed that the X-ray transparency was improved in spite of equivalent bending rigidity in the X-ray irradiation surface. From comparison between the mammography apparatus imaging table 1I and the mammography apparatus imaging table 1J, it was confirmed that unevenness of density in the X-ray irradiation surface was reduced. The X-ray irradiation surface of each of the mammography apparatus imaging table 1J and the mammography apparatus imaging table 1K was polished with sand paper to expose the carbon fibers. When the surface was traced with a bare hand, fluff of the carbon fibers hitched fingers to give a feeling of pain in the mammography apparatus imaging table 1J. However, there was no feeling of pain in the mammography apparatus imaging table 1K. In addition, in the mammography apparatus imaging tables 1M and 1N, as compared with the mammography apparatus imaging table 1H, it was confirmed that excellent X-ray transparency and excellent bending rigidity in the X-ray irradiation surface were exhibited.

TABLE 1

| | | Example 1 Uni-directional | Example 2 Uni-directional + woven | Example 3 Uni-directional | Example 4 Uni-directional + woven | Example 5 Uni-directional | Comp. 1 Woven |
|---|---|---|---|---|---|---|---|
| Form of carbon fiber | | | | | | | |
| Aluminum equivalent of X-ray irradiation surface [mmAL] | 60 kV | 0.17 | 0.18 | 0.17 | 0.18 | 0.17 | 0.20 |
| | 20 kV | 0.14 | 0.15 | 0.14 | 0.15 | 0.14 | 0.16 |
| Bending elastic modulus of X-ray irradiation surface: Eb [GPa] | | 73 | 75 | 74 | 76 | 72 | 48 |
| Density of X-ray irradiation surface: ρ [g/cm$^3$] | | 1.54 | 1.53 | 1.55 | 1.54 | 1.55 | 1.48 |
| Specific bending elastic modulus of X-ray irradiation surface | | 2.70 | 2.75 | 2.71 | 2.75 | 2.68 | 2.46 |

TABLE 2

| Form of carbon fiber | | Ex. 11 Woven | Ex. 12 Woven | Ex. 13 Uni-directional | Ex. 14 Uni-directional | Ex. 15 Uni-directional + woven | Comp. Ex. 11 Woven | Ex. 16 Uni-directional | Ex. 17 Woven |
|---|---|---|---|---|---|---|---|---|---|
| Aluminum equivalent of X-ray | 60 kV | 0.19 | 0.19 | 0.12 | 0.12 | 0.13 | 0.20 | 0.12 | 0.10 |
| irradiation surface [mmAL] | 20 kV | 0.15 | 0.15 | 0.11 | 0.10 | 0.12 | 0.16 | 0.10 | 0.09 |
| Bending elastic modulus of X-ray irradiation surface: Eb [GPa] | | 42 | 43 | 45 | 46 | 44 | 48 | 49 | 10 |
| Density of X-ray irradiation surface: $\rho$ [g/cm$^3$] | | 1.18 | 1.20 | 0.50 | 0.48 | 0.56 | 1.48 | 0.47 | 0.19 |
| Specific bending elastic modulus of X-ray irradiation surface | | 2.93 | 2.93 | 7.13 | 7.54 | 6.32 | 2.46 | 7.70 | 11.1 |
| Ratio between major diameter and minor diameter of closed cell [—] | | — | — | 0.58 | 0.75 | 0.62 | — | — | — |
| Average minor diameter of closed cell [μm] | | — | — | 123 | 209 | 178 | — | — | — |
| Angle between minor axis of closed cell and thickness-direction axis [°] | | — | — | 53 | 24 | 18 | — | — | — |

INDUSTRIAL APPLICABILITY

According to the present invention, it is possible to provide an imaging table for mammography, which is thin in thickness and high in rigidity. In the imaging table, X-ray transparency can be improved to reduce the exposure dose of an examinee due to the thin thickness, and deflection caused by a load applied during imaging can be reduced due to the high rigidity. Thus, accuracy of a taken image is improved. In addition, the imaging table includes a resin sheet so that the X-ray transparency can be improved to reduce the exposure dose of the examinee, and the imaging table includes a skin material including a carbon fiber composite material so that high rigidity can be expressed to reduce the deflection caused by the load applied during the imaging. Thus, the accuracy of the taken image is improved.

While the present invention has been described in detail and with reference to specific embodiments thereof, it will be apparent to one skilled in the art that various changes and modifications can be made therein without departing from the spirit and scope thereof.

REFERENCE SIGNS LIST 1 mammography apparatus imaging table
2 mammography apparatus body
3 pressing plate
4 X-ray generation portion
5 X-ray irradiation surface
6 bottom surface of mammography apparatus imaging table
7 standing wall portion
8 opening portion
9 single-surface mold
10 surface A
11 surface B
12 surface C
13 unidirectional carbon fiber prepreg
14 coupling member
15 prepreg laminate
16 flexible film
17 bleeder
18 seal material
19 valve
20 female mold
21 male mold
22 first member
23 second member
24 carbon fiber woven fabric prepreg
25 resin sheet
26 step portion of top surface

The invention claimed is:

1. An imaging table for a mammography apparatus, which is formed by a planar body and is to be supported in a cantilever state on a body of the mammography apparatus, wherein an X-ray irradiation surface in the planar body is formed by a skin material and a resin sheet, the skin material comprising a carbon fiber composite material containing continuous fibers and a matrix resin, the resin sheet comprising a resin having lower density than that of the carbon fiber composite material being disposed on an inner layer side from the skin material.

2. The imaging table for a mammography apparatus according to claim 1, wherein at least the X-ray irradiation surface in the planar body is formed by a sandwich structure in which the skin material is disposed on each of opposite sides of a core material composed of the resin sheet.

3. The imaging table for a mammography apparatus according to claim 1, wherein the resin sheet is a foam material.

4. The imaging table for a mammography apparatus according to claim 1, wherein the resin sheet includes discontinuous reinforced fibers dispersed at random, wherein a single filament of discontinuous reinforced fibers exists as less than 500 thin-fineness strands.

5. The imaging table for a mammography apparatus according to claim 1, wherein the resin sheet includes a resin, discontinuous reinforced fibers, and voids.

6. The imaging table for a mammography apparatus according to claim 1, wherein the skin material comprises a carbon fiber woven fabric composite material including a woven fabric of carbon fibers and a resin.

7. The imaging table for a mammography apparatus according to claim 1, wherein a coupling member to be connected to the body of the mammography apparatus is provided in a region formed by the carbon fiber composite material.

8. The imaging table for a mammography apparatus according to claim 1, further comprising a connection surface to be connected to the body of the mammography apparatus, wherein the connection surface includes an opening portion.

9. The imaging table for a mammography apparatus according to claim 1, wherein a specific bending elastic modulus of the carbon fiber composite material is 2.50 or higher:

(specific bending elastic modulus)=(bending elastic modulus)$^{1/3}$ x (density)$^{-1}$.

10. The imaging table for a mammography apparatus according to claim 1, further comprising a first member and a second member, the first member forming a top surface including the X-ray irradiation surface, the second member forming a bottom surface opposed to the X-ray irradiation surface, and a standing wall portion erectly provided in an outer circumference of the bottom surface.

11. The imaging table for a mammography apparatus according to claim 10, wherein the second member is made of at least one kind selected from the group consisting of metal, plastic, and elastomer.

12. A mammography apparatus comprising the body of the mammography apparatus and the imaging table for a mammography apparatus according to claim 1, the body and the imaging table being connected to each other.

13. A method for manufacturing the imaging table for a mammography apparatus according to claim 1, comprising the following steps (I) and (II):

Step (I): a step of imparting a shape of a single-surface mold to a base material including carbon fibers (A) and a thermosetting resin (B), the carbon fibers including continuous fibers; and Step (II): a step of covering a space including the single-surface mold and the base material with a flexible film, and applying heat and pressure.

14. The method for manufacturing the imaging table for a mammography apparatus according to claim 13, wherein the shape of the single-surface mold is imparted to the base material by an automatic lamination apparatus.

\* \* \* \* \*